(12) United States Patent
Kanada

(10) Patent No.: US 9,613,187 B2
(45) Date of Patent: Apr. 4, 2017

(54) CLINICAL INFORMATION PROCESSING APPARATUS, METHOD AND PROGRAM

(71) Applicant: FUJIFILM CORPORATION, Tokyo (JP)

(72) Inventor: Shoji Kanada, Ashigarakami-gun (JP)

(73) Assignee: FUJIFILM CORPORATION, Tokyo (JP)

(*) Notice: Subject to any disclaimer, the term of this patent is extended or adjusted under 35 U.S.C. 154(b) by 101 days.

(21) Appl. No.: 13/650,905

(22) Filed: Oct. 12, 2012

(65) Prior Publication Data
US 2013/0096941 A1 Apr. 18, 2013

(30) Foreign Application Priority Data

Oct. 14, 2011 (JP) .................. 2011-226321

(51) Int. Cl.
G06Q 50/22 (2012.01)
G06F 19/00 (2011.01)
G06K 9/62 (2006.01)

(52) U.S. Cl.
CPC ........ *G06F 19/3443* (2013.01); *G06F 19/321* (2013.01); *G06K 9/6278* (2013.01)

(58) Field of Classification Search
CPC ...... G06Q 50/22; G06Q 50/24; G06F 19/321; G06F 19/3443
USPC .......................................................... 705/2
See application file for complete search history.

(56) References Cited

U.S. PATENT DOCUMENTS

| 5,940,802 A * | 8/1999 | Hildebrand et al. ............... 705/3 |
| 2004/0138926 A1* | 7/2004 | Ishikawa et al. .................. 705/2 |
| 2004/0193022 A1 | 9/2004 | Torii et al. |
| 2006/0241978 A1* | 10/2006 | Yoshii ............................... 705/3 |
| 2008/0076976 A1* | 3/2008 | Sakurai et al. ............... 600/300 |
| 2010/0198611 A1* | 8/2010 | Ruoff et al. ...................... 705/2 |
| 2010/0312798 A1 | 12/2010 | Dutta et al. |

(Continued)

FOREIGN PATENT DOCUMENTS

| JP | 2003-122845 A | 4/2003 |
| WO | WO 2009/083833 A1 | 7/2009 |

OTHER PUBLICATIONS

Extended European Search Report dated Jul. 2, 2014.

(Continued)

*Primary Examiner* — Lena Najarian
(74) *Attorney, Agent, or Firm* — McGinn IP Law Group, PLLC

(57) ABSTRACT

Likelihood ratio between a likelihood of belonging to one classification of a key item and a likelihood of belonging to other classification of the key item when a case belongs to each classification of a clinical-information item other than the key item is calculated, based on registration case information for calculating a likelihood ratio, for each classification of a key item. A weighting coefficient corresponding to each classification of the clinical-information item other than the key item for each classification of the key item is determined based on a target classification of a target clinical-information item and the calculated likelihood ratio. A degree of similarity is calculated for each registration case included in registration case information for calculating a degree of similarity by using weighting information corresponding to each classification of the key item and each classification of the clinical-information item other than the key item.

26 Claims, 17 Drawing Sheets

(56) References Cited

U.S. PATENT DOCUMENTS

2011/0099032 A1  4/2011  Miyasa et al.
2011/0288879 A1* 11/2011 Gice et al. .................. 705/2
2013/0006669 A1*  1/2013 Nakamura .................. 705/3

OTHER PUBLICATIONS

Huang, et al., "Integrating Data Mining with Case-Based Reasoning for Chronic Diseases Prognosis and Diagnosis" Expert Systems with Applications, Oxford, GB, vol. 32, No. 3, Nov. 17, 2006, pp. 856-867.

* cited by examiner

FIG. 3

REGISTRATION CASE INFORMATION

|  | DIAGNOSIS (DISEASE NAME) | AGE | FEVER | COUGH | SPUTUM | WBC | ... |
|---|---|---|---|---|---|---|---|
| CASE 1 | PNEUMOCOCCAL PNEUMONIA | 62 YEARS OLD | 38.9 | LOW GRADE | LOW GRADE | 11000 | ... |
| CASE 2 | MYCOPLASMA PNEUMONIA | 42 YEARS OLD | 38.5 | HIGH GRADE | LOW GRADE | 5300 | ... |
| CASE 3 | PULMONARY TUBERCULOSIS | 79 YEARS OLD | 37.2 | NONE | NONE | 6900 | ... |
| CASE 4 | DIFFUSE PANBRONCHIOLITIS | 68 YEARS OLD | 37.4 | LOW GRADE | HIGH GRADE | 7600 | ... |
| ... | ... | ... | ... | ... | ... | ... | ... |

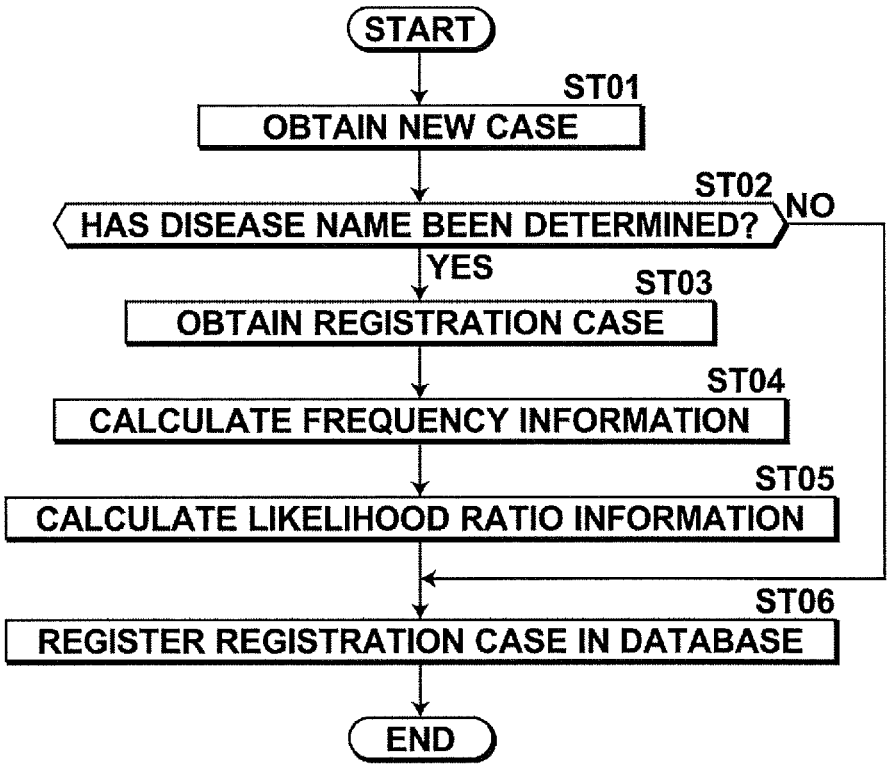
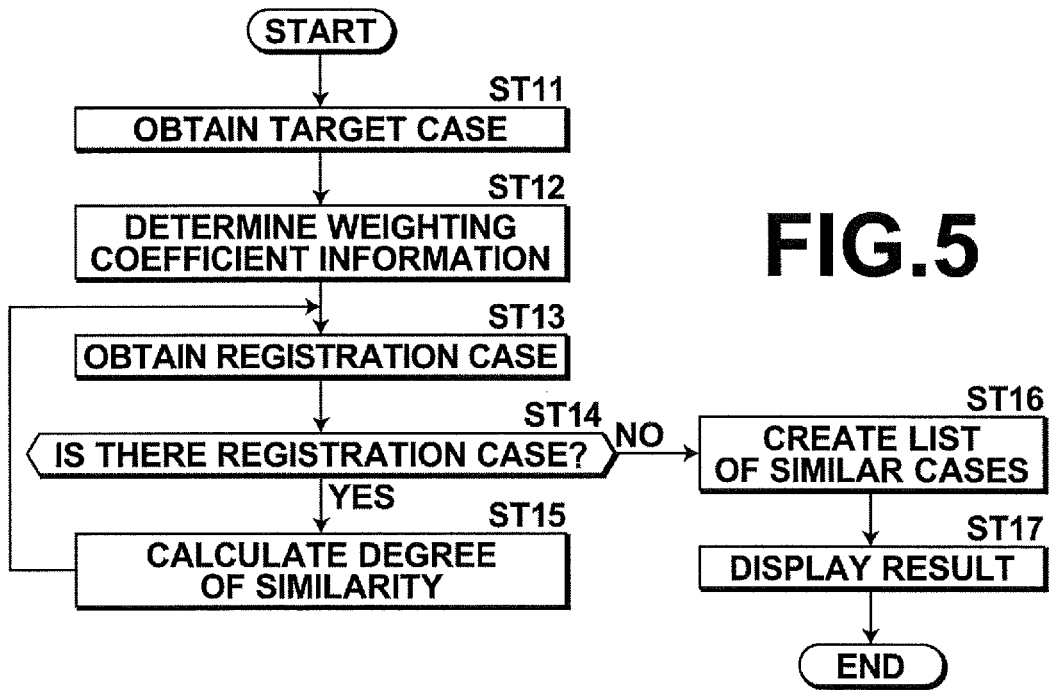

FIG.6

FREQUENCY INFORMATION

| | AGE | | | FEVER | | | COUGH | | | SPUTUM | | | WBC | | |
|---|---|---|---|---|---|---|---|---|---|---|---|---|---|---|---|
| | ~40 | 40~65 | 65~ | ~37 | 37~38 | 38~ | NONE | LOW GRADE | HIGH GRADE | NONE | LOW GRADE | HIGH GRADE | ~7900 | 7900~12000 | 12000~ |
| TOTAL NUMBER | 26 | 42 | 46 | 24 | 38 | 67 | 14 | 85 | 28 | 21 | 77 | 25 | 50 | 46 | 31 |
| PNEUMOCOCCAL PNEUMONIA | 0 | 6 | 9 | 2 | 1 | 13 | 1 | 13 | 2 | 1 | 14 | 0 | 3 | 5 | 8 |
| MYCOPLASMA | 16 | 5 | 0 | 0 | 1 | 20 | 0 | 4 | 17 | 5 | 12 | 3 | 11 | 10 | 0 |
| PULMONARY TUBERCULOSIS | 8 | 3 | 4 | 4 | 9 | 3 | 2 | 12 | 2 | 4 | 9 | 1 | 11 | 3 | 0 |
| DIFFUSE PANBRONCHIOLITIS | 0 | 3 | 8 | 6 | 5 | 1 | 0 | 9 | 2 | 1 | 3 | 8 | 5 | 4 | 3 |
| ... | | | | | | | | | | | | | | | |

FIG.7

LIKELIHOOD RATIO INFORMATION

| | AGE | | | FEVER | | | COUGH | | | SPUTUM | | | WBC | | |
|---|---|---|---|---|---|---|---|---|---|---|---|---|---|---|---|
| | ~40 | 40~65 | 65~ | ~37 | 37~38 | 38~ | NONE | LOW GRADE | HIGH GRADE | NONE | LOW GRADE | HIGH GRADE | ~7900 | 7900~12000 | 12000~ |
| PNEUMOCOCCAL PNEUMONIA | 0.1 | 1.2 | 1.7 | 0.7 | 0.2 | 1.7 | 0.6 | 1.2 | 0.6 | 0.6 | 1.2 | 0.6 | 0.4 | 0.8 | 2.4 |
| MYCOPLASMA | 8.1 | 0.7 | 0.1 | 0.1 | 0.2 | 2.2 | 0.1 | 0.3 | 7.8 | 1.6 | 1.0 | 0.7 | 1.4 | 1.4 | 0.2 |
| PULMONARY TUBERCULOSIS | 3.1 | 0.6 | 0.7 | 1.4 | 2.2 | 0.3 | 1.1 | 1.1 | 0.6 | 1.8 | 1.0 | 0.4 | 2.3 | 0.6 | 0.2 |
| DIFFUSE PANBRONCHIOLITIS | 0.1 | 0.8 | 2.0 | 3.2 | 1.5 | 0.2 | 0.2 | 1.2 | 0.9 | 0.5 | 0.4 | 4.3 | 1.1 | 0.9 | 1.0 |
| ... | | | | | | | | | | | | | | | |

FIG.8

WEIGHTING COEFFICIENT INFORMATION

| | AGE | | | FEVER | | | COUGH | | | SPUTUM | | | WBC | | |
|---|---|---|---|---|---|---|---|---|---|---|---|---|---|---|---|
| | ~40 | 40~65 | 65~ | ~37 | 37~38 | 38~ | NONE | LOW GRADE | HIGH GRADE | NONE | LOW GRADE | HIGH GRADE | ~7900 | 7900~12000 | 12000~ |
| PNEUMOCOCCAL PNEUMONIA | -2.3 | 0.2 | 0.2 | -0.4 | -1.6 | 0.5 | -0.5 | -0.5 | 0 | -0.5 | -0.5 | 0 | -0.9 | 0 | -0.2 |
| MYCOPLASMA | -0.4 | 0 | -2.3 | -2.3 | -1.6 | 0.8 | -2.3 | -1.2 | 2.1 | -0.4 | -0.4 | 0 | 0.3 | 0.3 | -1.6 |
| PULMONARY TUBERCULOSIS | -0.5 | 0 | -0.5 | -1.2 | -1.2 | 0 | -0.5 | -0.5 | 0 | -0.9 | -0.9 | 0 | -0.5 | 0 | -1.6 |
| DIFFUSE PANBRONCHIOLITIS | -2.3 | 0 | -0.2 | -1.6 | -1.6 | 0 | -1.6 | -0.1 | 0.0 | -0.7 | -0.9 | -0.9 | -0.1 | 0 | -0.1 |
| ... | | | | | | | | | | | | | | | |

FIG.9

DEGREE-OF-SIMILARITY DETERMINATION INFORMATION

| | DISEASE NAME | AGE | FEVER | COUGH | SPUTUM | WBC | DEGREE OF SIMILARITY OF CASE |
|---|---|---|---|---|---|---|---|
| CASE 1 | PNEUMOCOCCAL PNEUMONIA | 0.2 | 0.5 | -0.5 | -0.5 | 0 | -0.3 |
| CASE 2 | MYCOPLASMA PNEUMONIA | 0 | 0.8 | 2.1 | -0.4 | 0.3 | 2.8 |
| CASE 3 | PULMONARY TUBERCULOSIS | -0.5 | -1.2 | -0.5 | -0.9 | -0.5 | -3.6 |
| CASE 4 | DIFFUSE PANBRONCHIOLITIS | -1.6 | -1.6 | -0.1 | 1.5 | 0 | -1.8 |
| ... | ... | ... | ... | ... | ... | ... | ... |

FIG. 10

| DEGREE OF SIMILARITY | PATIENT'S INFORMATION | DIAGNOSIS NAME | TREATMENT · DRUG ADMINISTRATION | CHIEF COMPLAINT SUMMARY | EXAMINATION RESULT SUMMARY | IMAGE |
|---|---|---|---|---|---|---|
| 87 | 42 YEARS OLD, MAN | MYCOPLASMA PNEUMONIA | MACROLIDE | FEVER OF 38°C OR HIGHER, HIGH-GRADE COUGH | WBC11000, SpO2=97%, CRP=1.2 |  |
| 78 | 64 YEARS OLD, MAN | CHLAMYDIA PNEUMONIA | CARBAPENEM | FEVER OF BETWEEN 37°C AND 38°C, MALAISE | WBC8500, SpO2=96%, CRP=0.8 |  |
| 69 | 85 YEARS OLD, WOMAN | MYCOPLASMA PNEUMONIA | MACROLIDE | FEVER OF 38°C OR HIGHER | WBC12500, SpO2=95%, CRP=0.9 |  |
| 57 | 73 YEARS OLD, WOMAN | HAEMOPHILUS INFLUENZAE PNEUMONIA | PENICILLINS | HIGH-GRADE COUGH | WBC8800, SpO2=98%, CRP=1.7 |  |
| 55 | 69 YEARS OLD, MAN | PNEUMOCOCCAL PNEUMONIA | PENICILLINS | HIGH-GRADE COUGH, FEVER OF BETWEEN 37°C AND 38°C, HIGH-GRADE SPUTUM | WBC9500, SpO2=95%, CRP=2.0 |  |
| 51 | 60 YEARS OLD, WOMAN | PNEUMOCOCCAL PNEUMONIA | PENICILLINS | LOW-GRADE COUGH, FEVER OF BETWEEN 37°C AND 38°C | WBC10100, SpO2=93%, CRP=1.8 |  |
| 43 | 49 YEARS OLD, WOMAN | PNEUMOCOCCAL PNEUMONIA | CARBAPENEM | HIGH-GRADE COUGH, FEVER OF 38°C OR HIGHER, MALAISE | WBC12500, SpO2=95%, CRP=2.1 |  |
| 30 | 55 YEARS OLD, MAN | PNEUMOCOCCAL PNEUMONIA | CARBAPENEM | HIGH-GRADE COUGH, FEVER OF 38°C OR HIGHER, DIFFICULTY IN BREATHING | WBC15500, SpO2=92%, CRP=1.3 |  |

| PATIENT'S ID : 12345 | 42 YEARS OLD, MAN | MYCOPLASMA PNEUMONIA |
|---|---|---|
| FEVER : 38.5 | | |
| COUGH : HIGH GRADE | SPUTUM : LOW GRADE | |
| SpO2 : 97% | WBC : 11000 | CRP=1.2 |
| | | |

FIG.14

DISEASE NAME ESTIMATION INFORMATION

| | AGE 40~65 | FEVER ~38 | COUGH HIGH GRADE | SPUTUM HIGH GRADE | WBC 7900~12000 | OVERALL LIKELIHOOD RATIO |
|---|---|---|---|---|---|---|
| PNEUMOCOCCAL PNEUMONIA | 1.2 | 1.7 | 0.6 | 0.6 | 0.8 | 0.59 |
| MYCOPLASMA PNEUMONIA | 0.7 | 2.2 | 7.8 | 0.7 | 1.4 | 11.8 |
| PULMONARY TUBERCULOSIS | 0.6 | 0.3 | 0.6 | 0.4 | 0.6 | 0.03 |
| DIFFUSE PANBRONCHIOLITIS | 0.8 | 0.2 | 0.9 | 4.3 | 0.9 | 0.6 |
| ... | | | | | | |

FIG.17

| WEIGHTING COEFFICIENT INFORMATION | AGE | | FEVER | | | COUGH | | | SPUTUM | | | WBC | | |
|---|---|---|---|---|---|---|---|---|---|---|---|---|---|---|
| | ~40 | 40~65 | 65~ | ~37 | 37~38 | 38~ | NONE | LOW GRADE | HIGH GRADE | NONE | LOW GRADE | HIGH GRADE | ~7900 | 7900~12000 | 12000~ |
| MYCOPLASMA | -0.4 | 0 | -2.3 | -2.3 | -1.6 | 0.8 | -2.3 | -1.2 | 2.1 | -0.4 | -0.4 | 0 | 0.3 | 0.3 | -1.6 |

FIG.18

DEGREE-OF-SIMILARITY DETERMINATION INFORMATION

| | DISEASE NAME (NOT USED) | AGE | FEVER | COUGH | SPUTUM | WBC | DEGREE OF SIMILARITY OF CASE |
|---|---|---|---|---|---|---|---|
| CASE 1 | PNEUMOCOCCAL PNEUMONIA | 0 | 0.8 | -1.2 | -0.4 | -1.6 | -4.7 |
| CASE 2 | MYCOPLASMA PNEUMONIA | 0 | 0.8 | 2.1 | -0.4 | 0.3 | 2.8 |
| CASE 3 | PULMONARY TUBERCULOSIS | -2.3 | -1.6 | -2.3 | -0.4 | 0.3 | -6.4 |
| CASE 4 | DIFFUSE PANBRONCHIOLITIS | -2.3 | -1.6 | -1.2 | 0 | 0.3 | -4.8 |
| ... | ... | ... | ... | ... | ... | ... | |

CLINICAL INFORMATION PROCESSING APPARATUS, METHOD AND PROGRAM

BACKGROUND OF THE INVENTION

Field of the Invention

The present invention relates to a clinical information processing apparatus and method for calculating a degree of similarity between a case of a target patient and a case of a comparison target patient. Further, the present invention relates to a program for causing a computer to execute the clinical information processing method.

Description of the Related Art

In recent years, in medical fields, diagnosis assistance techniques utilizing various kinds of information obtained in examination and treatment of patients drew attention. Further, a technique for extracting, as reference information for diagnosing a disease name or determining a treatment policy of a target patient, a past case of a comparison target patient similar to a target patient's case is expected. The similar case of the comparison target patient is extracted by calculating degrees of similarity between the target patient's case and cases of comparison target patients based on various clinical-information items included in each case of past patients.

Japanese Unexamined Patent Publication No. 2003-122845 (Patent Document 1) proposes a method in which symptoms of a retrieval target case are input as a symptom list. Further, the input symptom list is converted into a symptom vector based on a criterion, such as presence and the grade of a symptom. Further, a degree of similarity between the symptom vector of the retrieval target and a symptom vector of each symptom registered in a symptom information database is calculated based on a total number of symptoms in which the two symptom vectors coincide with each other.

U.S. Patent Application Publication No. 20040193022 (Patent Document 2) proposes a method in which a degree of similarity of each case data to new patient data is calculated when the new patient data are input. The degree of similarity is calculated, as a sum of value groups obtained by weighting a difference between a value of case data and a value of the new patient data for each item based on the degree of influence of the value of the item in the new patient data. Further, a degree of similarity of each disease name is obtained as a sum of degrees of similarity of case data having the disease name, and a disease name in which the degree of similarity is the highest is displayed together with a value of an item in the new patient data used in calculation of the degree of similarity, and the degree of influence of which is the highest.

However, since there are various kinds of clinical-information items, and symptoms include the clinical-information items in various combinations, there are so many kinds of symptoms. Therefore, when symptom data managed by each hospital or the like are arranged for each disease name or the like, the number of cases for each disease name often tends to be small. With respect to clinical-information items, the method disclosed in Patent Document 1 can evaluate, as a case of a high degree of similarity, a case in which most of information coincides if such a case exists. However, since weighting on each symptom is not considered, if only cases in which information slightly coincides exist, it is impossible to appropriately evaluate the degree of similarity.

Meanwhile, the method disclosed in Patent Document 2 calculates a degree of similarity based on a probability (a conditional probability) of belonging to each disease name when each clinical-information item, such as an age, belongs to a predetermined value. The method calculates the degree of similarity based on the degree of influence for judging a disease name for each clinical-information item and information about a difference between a value of case data and a value of the new patient data. However, in the method of Patent Document 2, the degree of influence of each clinical-information item is the same regardless of the disease name. Therefore, it is impossible to accurately calculate a degree of similarity based on the characteristic of each clinical-information item. Further, with respect to values of various clinical-information items, it is not always appropriate to simply evaluate a degree of similarity only based on a difference between values of clinical-information items of case data and those of new patient data. It is not appropriate to evaluate the degree of similarity in such a manner when it is important to judge whether the value of a clinical-information item belongs to a standard range that is considered to be normal in medical diagnosis, or when values of the clinical-information items change nonlinearly. Therefore, the degree of similarity calculated by using the method disclosed in Patent Document 2 is not accurate, and the method is not practical.

SUMMARY OF THE INVENTION

In view of the foregoing circumstances, it is an object of the present invention to provide a practical clinical information processing apparatus, method and program that can calculate degrees of similarity between a target patient's case and past cases of comparison target patients by appropriately performing weighting based on each clinical-information item even when the number of the past cases of comparison target patients is small.

A clinical information processing apparatus according to a first aspect of the present invention is a clinical information processing apparatus comprising:

a registration case information obtainment unit that obtains registration case information for calculating a likelihood ratio including a multiplicity of registration cases about a plurality of comparison target patients, and to each of the multiplicity of registration cases a plurality of clinical-information items each of which is classifiable into a plurality of groups being correlated, and registration case information for calculating a degree of similarity including a multiplicity of registration cases about a plurality of comparison target patients, and to each of the multiplicity of registration cases a plurality of clinical-information items each of which is classifiable into a plurality of groups being correlated;

a target case obtainment unit that obtains, as a target classification of a target clinical item, a classification of each of a plurality of clinical-information items about a target patient;

a likelihood ratio information calculation unit that calculates, based on the registration case information for calculating a likelihood ratio, likelihood ratio information for each classification of a key item of the plurality of clinical-information items, and the likelihood ratio information correlating a likelihood ratio corresponding to each classification of at least one clinical-information item other than the key item to each classification of the key item included in the registration cases, and the likelihood ratio information being obtained by calculating a likelihood ratio between a likelihood of belonging to one classification of the key item and a likelihood of belonging to any classification of the key item other than the one classification of the key item when a case belongs to each classification of the at least one clinical-information item other than the key item;

a weighting coefficient determination unit that determines, based on the target classification of the target clinical-information item and the likelihood ratio information, weighting coefficient information in which a weighting coefficient corresponding to each classification of the at least one clinical-information item other than the key item is correlated to each classification of the key item; and a degree-of-similarity calculation unit that specifies, based on the determined weighting coefficient information, the weighting coefficient corresponding to each classification of the key item and each classification of at least one clinical-information item other than the key item for each of the registration cases included in the registration case information for calculating a degree of similarity, and that calculates a degree of similarity by using the specified weighting coefficient.

A clinical information processing method according to a first aspect of the present invention is a clinical information processing method, the method comprising the steps of:

obtaining registration case information for calculating a likelihood ratio including a multiplicity of registration cases about a plurality of comparison target patients, and to each of the multiplicity of registration cases a plurality of clinical-information items each of which is classifiable into a plurality of groups being correlated, and registration case information for calculating a degree of similarity including a multiplicity of registration cases about a plurality of comparison target patients, and to each of the multiplicity of registration cases a plurality of clinical-information items each of which is classifiable into a plurality of groups being correlated;

obtaining, as a target classification of a target clinical item, a classification of each of a plurality of clinical-information items about a target patient;

calculating, based on the registration case information for calculating a likelihood ratio, likelihood ratio information for each classification of a key item of the plurality of clinical-information items, and the likelihood ratio information correlating a likelihood ratio corresponding to each classification of at least one clinical-information item other than the key item to each classification of the key item included in the registration cases, and the likelihood ratio information being obtained by calculating a likelihood ratio between a likelihood of belonging to one classification of the key item and a likelihood of belonging to any classification of the key item other than the one classification of the key item when a case belongs to each classification of the at least one clinical-information item other than the key item;

determining, based on the target classification of the target clinical-information item and the likelihood ratio information, weighting coefficient information in which a weighting coefficient corresponding to each classification of the at least one clinical-information item other than the key item is correlated to each classification of the key item; and specifying, based on the determined weighting coefficient information, the weighting coefficient corresponding to each classification of the key item and each classification of at least one clinical-information item other than the key item for each of the registration cases included in the registration case information for calculating a degree of similarity, and calculating a degree of similarity by using the specified weighting coefficient.

A clinical information processing program according to an aspect of the present invention is a clinical information processing program for causing a computer to function as:

a registration case information obtainment unit that obtains registration case information for calculating a likelihood ratio including a multiplicity of registration cases about a plurality of comparison target patients, and to each of the multiplicity of registration cases a plurality of clinical-information items each of which is classifiable into a plurality of groups being correlated, and registration case information for calculating a degree of similarity including a multiplicity of registration cases about a plurality of comparison target patients, and to each of the multiplicity of registration cases a plurality of clinical-information items each of which is classifiable into a plurality of groups being correlated;

a target case obtainment unit that obtains, as a target classification of a target clinical item, a classification of each of a plurality of clinical-information items about a target patient;

a likelihood ratio information calculation unit that calculates, based on the registration case information for calculating a likelihood ratio, likelihood ratio information for each classification of a key item of the plurality of clinical-information items, and the likelihood ratio information correlating a likelihood ratio corresponding to each classification of at least one clinical-information item other than the key item to each classification of the key item included in the registration cases, and the likelihood ratio information being obtained by calculating a likelihood ratio between a likelihood of belonging to one classification of the key item and a likelihood of belonging to any classification of the key item other than the one classification of the key item when a case belongs to each classification of the at least one clinical-information item other than the key item;

a weighting coefficient determination unit that determines, based on the target classification of the target clinical-information item and the likelihood ratio information, weighting coefficient information in which a weighting coefficient corresponding to each classification of the at least one clinical-information item other than the key item is correlated to each classification of the key item; and a degree-of-similarity calculation unit that specifies, based on the determined weighting coefficient information, the weighting coefficient corresponding to each classification of the key item and each classification of at least one clinical-information item other than the key item for each of the registration cases included in the registration case information for calculating a degree of similarity, and that calculates a degree of similarity by using the specified weighting coefficient.

A clinical information processing apparatus according to a second aspect of the present invention is a clinical information processing apparatus comprising:

a registration case information obtainment unit that obtains registration case information for calculating a likelihood ratio including a multiplicity of registration cases about a plurality of comparison target patients, and to each of the multiplicity of registration cases a plurality of clinical-information items each of which is classifiable into a plurality of groups being correlated, and registration case information for calculating a degree of similarity including a multiplicity of registration cases about a plurality of comparison target patients, and to each of the multiplicity of registration cases a plurality of clinical-information items each of which is classifiable into a plurality of groups being correlated, and registration case information for estimating a key item including a multiplicity of registration cases about a plurality of comparison target patients, and to each of the multiplicity of registration cases a plurality of clinical-information items each of which is classifiable into a plurality of groups being correlated;

a target case obtainment unit that obtains, as a target classification of a target clinical item, a classification of each of a plurality of clinical-information items about a target patient;

a likelihood ratio information calculation unit that calculates, based on the registration case information for calculating a likelihood ratio, likelihood ratio information for each classification of a key item of the plurality of clinical-information items, and the likelihood ratio information correlating a likelihood ratio corresponding to each classification of at least one clinical-information item other than the key item to each classification of the key item included in the registration cases, and the likelihood ratio information being obtained by calculating a likelihood ratio between a likelihood of belonging to one classification of the key item and a likelihood of belonging to any classification of the key item other than the one classification of the key item when a case belongs to each classification of the at least one clinical-information item other than the key item;

a key item estimation unit that tentatively estimates a classification of the key item to which the target patient is estimated to belong based on the target classification of the target clinical-information information item and the registration case information for estimating a key item;

a weighting coefficient determination unit that determines, based on the estimated classification of the key item and the target classification of the target clinical-information item, weighting coefficient information in which a weighting coefficient corresponding to each classification of the at least one clinical-information item other than the key item is correlated to the estimated classification of the key item; and a degree-of-similarity calculation unit that specifies, based on the determined weighting coefficient information, the weighting coefficient corresponding to each classification of the at least one clinical-information items other than the key item for each of the registration cases included in the registration case information for calculating a degree of similarity, and that calculates a degree of similarity by using the specified weighting coefficient.

In the first and second aspects of the present invention, the clinical-information item is information about patients obtained for diagnosis. The clinical-information item is obtained by being reported by the patients, or by examining the patients and the like. The clinical-information items are, for example, patient's basic information, chief complaint, life history, an anamnesis, family history, various kinds of examination result data, various findings based on images, feature values of images, the content of performed drug administration and treatment, a treatment result, genetic information, a disease name, severity, and the like. A key item is one of the clinical-information items. The key item is information used as a key for judging the degree of similarity.

The registration case information for calculating a likelihood ratio and the registration case information for calculating a degree of similarity may overlap or coincide with each other. Alternatively, they may be different from each other.

In the first and second aspects of the present invention, classifications of the clinical-information item are groups to which a clinical-information item is classified based on a judgment standard on medical diagnosis. The clinical-information item is classified into groups based on a type and a numerical value range. The clinical-information item may be classified into groups, for example, based on an evaluation value of white blood cell number in a blood test, i.e., whether the number is within a normal range or not. Alternatively, the clinical-information item may be classified into groups based on the kind of a disease (a disease name or the like).

In the first and second aspects of the present invention, the expression "calculates a degree of similarity by using the weighting coefficient" means that any method may be used as long as a large weighting coefficient is calculate as a degree of similarity. For example, a sum of weighting coefficients may be used to calculate the degree of similarity. Alternatively, a distance defined by a sum of squares or the like of a difference between a weighting coefficient of a classification of each clinical-information item of a target patient and a weighting coefficient of a classification of each clinical-information item of registration cases may be calculated as a degree of similarity. Further, the degree of similarity may be judged to be higher as the distance is shorter.

In the first aspect of the present invention, it is desirable that the weighting coefficient determination unit determines the weighting coefficient in such a manner that the weighting coefficient becomes larger as the likelihood ratio corresponding to the target classification of the target clinical-information item is higher.

The expression "determines the weighting coefficient in such a manner that the weighting coefficient becomes larger as the likelihood ratio is higher" means that any method may be used to determine the weighting coefficient as long as the weighting coefficient becomes larger as the likelihood ratio is higher. For example, the weighting coefficient may continuously become larger based on the likelihood ratio. Alternatively, the weighting coefficient may intermittently become larger. Further, the weighting coefficient may be determined for each clinical-information item in such a manner that weighting on a target classification and weighting on a classification or classifications other than the target classification differ from each other. For example, when each weighting coefficient is determined as a positive value, each weighting coefficient may be determined in such a manner that the value of each weighting coefficient becomes larger as the likelihood ratio is higher. In contrast, when each weighting coefficient is determined as a negative value, each weighting coefficient may be determined in such a manner that the value of each weighting coefficient becomes smaller (the absolute value of the negative value is larger) as the likelihood ratio is lower.

It is desirable that the weighting coefficient determination unit in the first aspect of the present invention performs weighting in such a manner that the weighting coefficient becomes larger based on the likelihood ratio when the likelihood ratio corresponding the target classification of the target clinical-information item is greater than or equal to a first threshold value, and that the weighting coefficient becomes smaller based on the likelihood ratio when the likelihood ratio corresponding the target classification of the target clinical-information item is less than a second threshold value.

An arbitrary numerical value may be set as the first threshold value as long as the first threshold value can evaluate, based on the value of a likelihood ratio, that the degree of relationship of a classification of a clinical-information item with a classification of a key item is substantially high (when the clinical-information item is classified into a certain group, a Probability of belonging to the classification of the key item). It is desirable that the first threshold value is larger than or equal to 1 and less than or equal to 2. For example, 1 is appropriate as the first threshold value.

An arbitrary numerical value may be set as the second threshold value as long as the second threshold value is less than or equal to the first threshold value, and can evaluate, based on the value of a likelihood ratio, that the degree of relationship of a classification of a clinical-information item with a classification of a key item is substantially low (when the clinical-information item is classified into a certain group, a probability of belonging to the classification of the key item). It is desirable that the second threshold value is larger than or equal to 0.5 and less than or equal to 1. For example, 1 is appropriate as the second threshold value.

Further, it is desirable that the weighting coefficient determination unit according to the first aspect of the present invention performs weighting in such a manner that when a likelihood ratio corresponding the target classification of the target clinical-information item is greater than or equal to a third threshold value and a likelihood ratio corresponding to a classification other than the target classification of the clinical-information item is greater than or equal to the third threshold value, the weighting coefficient corresponding to the classification other than the target classification of the clinical-information item becomes larger based on the likelihood ratios, and that when at least one of the likelihood ratio corresponding the target classification of the target clinical-information item and the likelihood ratio corresponding to the classification other than the target classification of the clinical-information item is less than a fourth threshold value, the weighting coefficient corresponding to the classification other than the target classification of the clinical-information item becomes smaller.

In the aforementioned case, the weighting coefficient determination unit may perform weighting in such a manner that the weighting coefficient corresponding to the classification other than the target classification of the target clinical-information item becomes a negative value when at least one of the likelihood ratio corresponding the target classification of the target clinical-information item and the likelihood ratio corresponding to the classification other than the target classification of the clinical-information item is less than the fourth threshold value.

An arbitrary numerical value may be set as the third threshold value as long as the third threshold value can evaluate, based on the value of a likelihood ratio, that the degree of relationship of a classification of a clinical-information item with a classification of a key item is substantially large (when the clinical-information item is classified into a certain group, a probability of belonging to the classification of the key item). It is desirable that the third threshold value is larger than or equal to 1 and less than or equal to 2. For example, 1 is appropriate as the third threshold value.

An arbitrary numerical value may be set as the fourth threshold value as long as the fourth threshold value is less than or equal to the third threshold value, and can evaluate, based on the value of a likelihood ratio, that the degree of relationship of a classification of a clinical-information item with a classification of a key item is substantially small (when the clinical-information item is classified into a certain group, a probability of belonging to the classification of the key item). It is desirable that the fourth threshold value is larger than or equal to 0.5 and less than or equal to 1. For example, 1 is appropriate as the fourth threshold value.

It is desirable that the weighting coefficient determination unit according to the first aspect of the present invention determines, for each classification of at least a part of the at least one clinical-information item other than the key item, a value obtained by performing logarithmic transformation on the likelihood ratio corresponding to each classification of the at least one clinical-information item other than the key item, as the weighting coefficient.

Further, it is desirable that the degree-of-similarity calculation unit according to the first aspect of the present invention includes a degree-of-similarity calculation case extraction unit that extracts, as a registration case for calculating a degree of similarity, only a registration case satisfying a predetermined condition in the registration case information for calculating a degree of similarity, and that the degree of similarity is calculated only based on the extracted registration case for calculating a degree of similarity.

As the "predetermined condition", an arbitrary condition may be set based on a demand of a user. For example, the predetermined condition may be a condition that a case corresponds to a predetermined disease name specified by an input by a user.

Further, when the degree-of-similarity calculation unit according to the first aspect of the present invention includes a degree-of-similarity calculation case extraction unit for extracting, as registration cases for calculating a degree of similarity, only registration cases satisfying a predetermined condition from the registration case information for calculating a degree of similarity, it is desirable that the registration case information obtainment unit according to the first aspect of the present invention further obtains registration case information for estimating a key item, and the registration case information including a multiplicity of registration cases each of which is correlated to a plurality of clinical-information items about a plurality of comparison target patients, as clinical-information items each of which is classifiable into a plurality of groups. Further, it is desirable that the apparatus further includes a key item estimation unit that estimates, based on the target classification of the target clinical-information item and the registration case information for estimating a key item, a classification of the key item to which the target patient is estimated to belong, and that the degree-of-similarity calculation case extraction unit extracts, as the registration case for calculating a degree of similarity, only the registration case correlated to the classification of the key item estimated by the key item estimation unit from the registration case information for calculating a degree of similarity.

The registration case information for estimating a key item may overlap or coincide with the registration case information for calculating a likelihood ratio or the registration case information for calculating a degree of similarity. Alternatively, the registration case information for estimating a key item may be different from the registration case information for calculating a likelihood ratio and the registration case information for calculating a degree of similarity.

Further, when the degree-of-similarity calculation unit according to the first aspect of the present invention includes a degree-of-similarity calculation case extraction unit for extracting, as registration cases for calculating a degree of similarity, only registration cases satisfying a predetermined condition from the registration case information for calculating a degree of similarity, the degree-of-similarity calculation case extraction unit may extract, based on the likelihood ratio information, only the registration case in which at least a likelihood ratio corresponding to a classification of each clinical-information item is greater than or equal to a fifth threshold value, as the registration case for calculating a degree of similarity, from the registration cases for calculating a degree of similarity.

The fifth threshold value may be an arbitrary value set based on an environment in which a clinical information processing apparatus is used and various demands of each user.

Further, when the degree-of-similarity calculation unit according to the first aspect of the present invention includes a degree-of-similarity calculation case extraction unit for extracting, as registration cases for calculating a degree of similarity, only registration cases satisfying a predetermined condition from the registration case information for calculating a degree of similarity, the degree-of-similarity calculation case extraction unit may extract, based on the likelihood ratio information, only the registration case correlated to a classification of a clinical-information item the likelihood ratio of which is ranked higher than or equal to a predetermined rank in descending order of values, as the registration case for calculating a degree of similarity, from the registration cases for calculating a degree of similarity.

The "predetermined rank" may be set arbitrarily based on an environment in which a clinical information processing apparatus is used and various demands of each user.

Further, it is desirable that the likelihood ratio information calculation unit according to the first or second aspect of the present invention includes a likelihood ratio calculation case extraction unit that extracts only the registration case satisfying an additional predetermined condition, as the registration case for calculating the likelihood ratio, from the registration case information for calculating a likelihood ratio, and calculates the likelihood ratio information only based on the extracted registration case for calculating the likelihood ratio.

In the aforementioned case, the clinical information processing apparatus according to the first or second aspect of the present invention may set an arbitrary condition based on a demand of a user, as the "additional predetermined condition". For example, the predetermined condition may be a condition that a case corresponds to a predetermined disease name specified by an input by a user. Further, the registration case information obtainment unit may further obtain registration case information for estimating a key item, and the registration case information including a multiplicity of registration cases about a plurality of comparison target patients, and to each of the multiplicity of registration cases a plurality of clinical-information items each of which is classifiable into a plurality of groups being correlated. Further, the apparatus may further include a key item estimation unit that tentatively estimates, based on the target classification of the target clinical-information item and the registration case information for estimating a key item, a classification of the key item to which the target patient is estimated to belong, and the likelihood ratio calculation case extraction unit may extract, as the registration case for calculating a likelihood ratio, only the registration case correlated to the classification of the key item estimated by the key item estimation unit from the registration case information for calculating a likelihood ratio.

In the first or second aspect of the present invention, it is desirable that each classification of the key item represents a disease name.

In the first or second aspect of the present invention, the degree-of-similarity calculation unit may calculate a degree of similarity for each disease name constituting complications by obtaining a weighting coefficient corresponding to each classification of the at least one clinical-information item other than the key item correlated to the complications when the disease name of the registration case is the complications, and obtain a highest one of calculated degrees of similarity, as a degree of similarity corresponding to the complications.

Further, in the first or second aspect of the present invention, the degree-of-similarity calculation unit may obtain a weighting coefficient corresponding to each classification of the at least one clinical-information item other than the key item correlated to complications for each disease name constituting the complications when the disease name of the registration case is the complications, and calculate a degree of similarity by using a largest one of weighting coefficients calculated for respective disease names constituting the complications, as a weighting coefficient corresponding to each classification of the at least one clinical-information item other than the key item.

In the first or second aspect of the present invention, it is desirable that the likelihood ratio information calculation unit further obtains a superordinate disease name of the disease name when the number of a registration case or cases correlated to the disease name is less than a predetermined number based on the registration case information for calculating a likelihood ratio, and calculates the likelihood ratio information by using the superordinate disease name instead of the disease name for the registration case correlated to the disease name.

Further, in the first or second aspect of the present invention, it is desirable that a clinical information processing apparatus further includes a display control unit that displays, based on the calculated degree of similarity, the registration cases as a list in descending order of the degree of similarity in such a manner to include information about the classification of the clinical-information items in which at least one of the likelihood ratio and the weighting coefficient is higher than or equal to a predetermined value for each of the registration cases.

The "information about the classification of the clinical-information items" may be any kind of information as long as the information represents a classification to which a value or a type represented in each of the clinical-information items belongs. For example, the information about the classification of the clinical-information items may be a disease name, each examination value, or the like of each of the clinical-information items. Alternatively, the information about the classification of the clinical-information items may be a classification to which a value or a type represented by each of the clinical-information items belongs.

Further, an arbitrary numerical value may be set as the predetermined value as long as the predetermined value can evaluate, based on the value of a likelihood ratio, that the degree of relationship of a classification of a clinical-information item with a classification of a key item is substantially high (when the clinical-information item is classified into a certain group, a probability of belonging to the classification of the key item). It is desirable that the likelihood ratio is greater than or equal to 2. For example, it is desirable that the predetermined value is 3.

According to the present invention, a likelihood ratio is calculated, based on registration case information for calculating a likelihood ratio, for each classification of a key item correlated to registration cases. With respect to each classification of at least one clinical-information item other than the key item included in the registration cases, a likelihood ratio between a likelihood of belonging to one classification of the key item and each classification of the at least one clinical-information item other than the key item and a likelihood of belonging to any classification of the key item other than the one classification of the key item and each classification of the at least one clinical-information item other than the key item is calculated. Further, each weighting coefficient is determined, based on the target classification of the target clinical-information item of the target patient and the likelihood ratio information, for each classification of the key item with respect to each classification of the at least one clinical-information item other than the key item. Therefore, it is possible to determine a weighting coefficient only if there are a small number of cases that are sufficient to judge the distribution of classifications of the clinical-information items. Even if the number of cases is relatively small, it is possible to accurately calculate a degree of similarity. Further, it is possible to appropriately determine the weighting coefficient in such a manner to reflect the degree of relationship of the classification of each of the clinical-information items with the classification of the key item. Hence, it is possible to accurately calculate a degree of similarity.

Note that the program of the present invention may be provided being recorded on a computer readable medium. Those who are skilled in the art would know that computer readable media are not limited to any specific type of device, and include, but are not limited to: floppy disks, CD's, RAM's, ROM's, hard disks, magnetic tapes, and internet downloads, in which computer instructions can be stored and/or transmitted. Transmission of the computer instructions through a network or through wireless transmission means is also within the scope of this invention. Additionally, computer instructions include, but are not limited to: source, object and executable code, and can be in any language including higher level languages, assembly language, and machine language.

BRIEF DESCRIPTION OF THE DRAWINGS

FIG. 3 is a diagram illustrating an example of registration case information in first through third embodiments;

FIG. 4 is a flow chart illustrating a flow of clinical information processing in the first through third embodiments (No. 1);

FIG. 5 is a flow chart illustrating a flow of clinical information processing in the first embodiment (No. 2);

FIG. 6 is a diagram illustrating an example of frequency information in the first through third embodiments;

FIG. 7 is a diagram illustrating an example of likelihood ratio information in the first through third embodiments;

FIG. 8 is a diagram illustrating an example of weighting coefficient information in the first embodiment;

FIG. 9 is a diagram illustrating an example of degree-of-similarity determination information in the first embodiment;

FIG. 10 is a diagram illustrating an example of display of a similar case extraction result in the first through third embodiments (list display);

FIG. 14 is a diagram illustrating an example of disease name estimation information in the second embodiment;

FIG. 17 is a diagram illustrating an example of weighting coefficient information in the third embodiment; and FIG. 18 is a diagram illustrating an example of degree-of-similarity determination information in the third embodiment.

DESCRIPTION OF THE PREFERRED EMBODIMENTS

Figure 1:
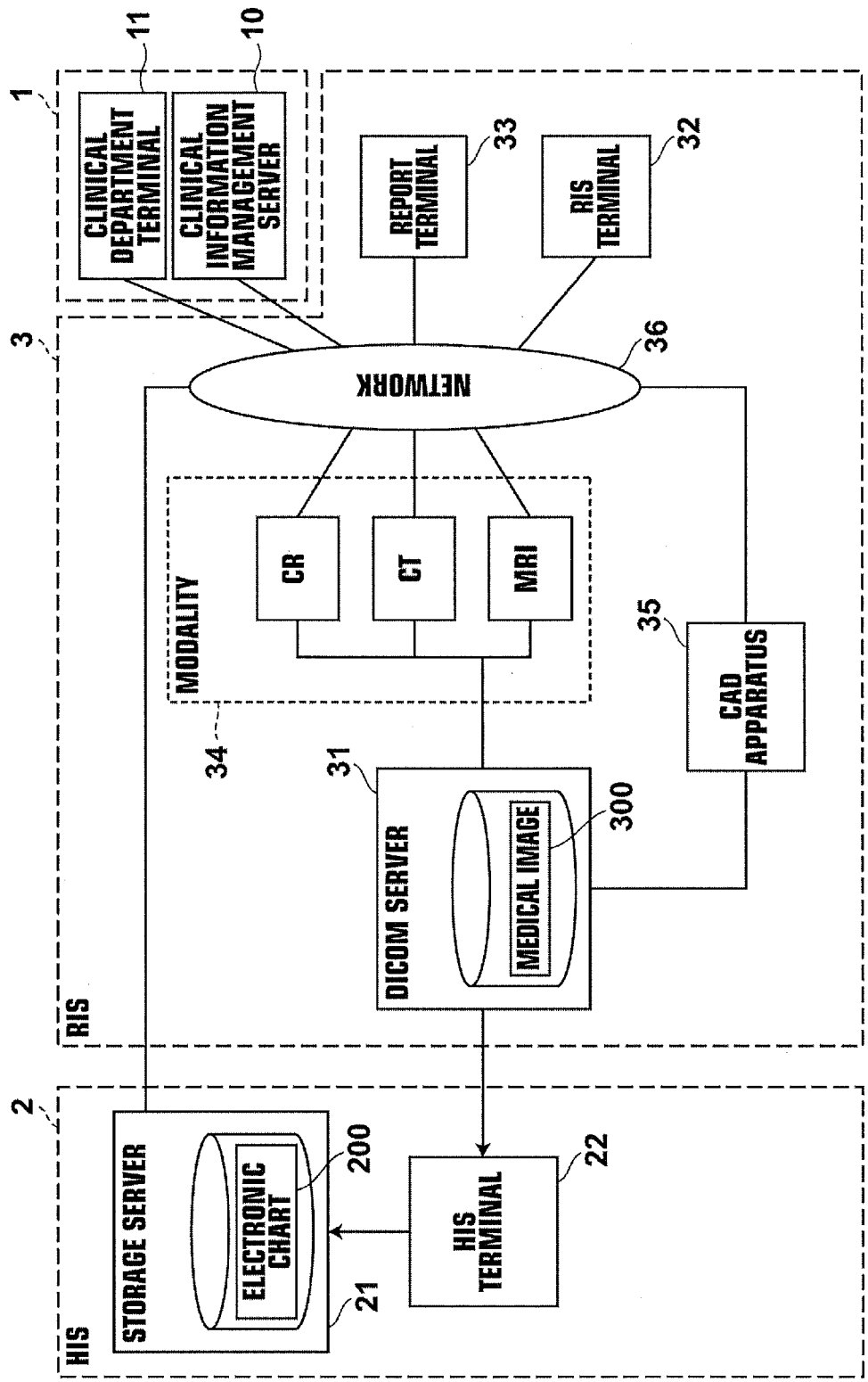
FIG. 1 is a schematic diagram illustrating the configuration of a medical information system to which a clinical information processing apparatus according to an embodiment of the present invention has been applied.
Figure 2:
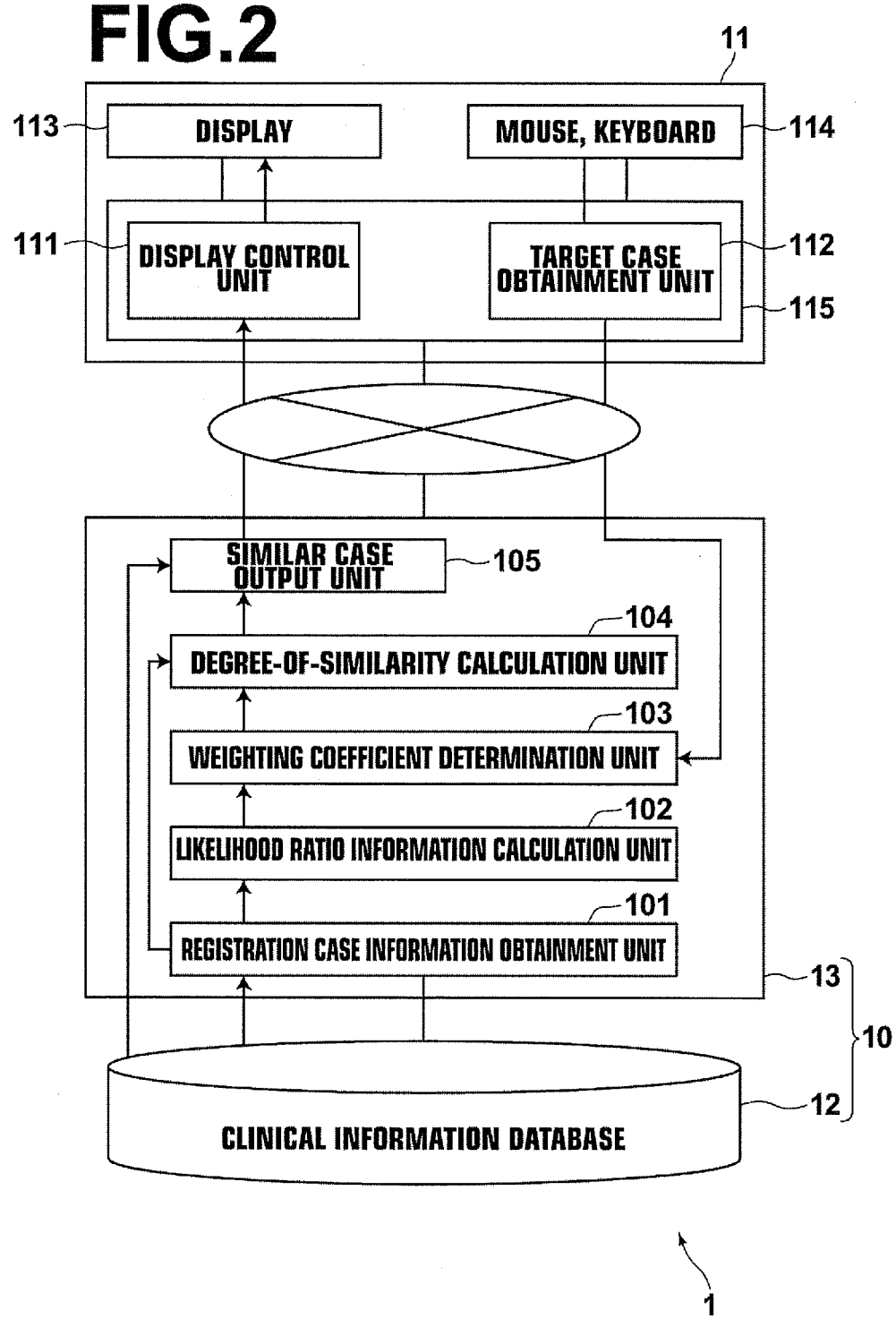
FIG. 2 is a functional block diagram of a clinical information processing apparatus according to a first embodiment.

Embodiments of a diagnosis assistance apparatus of the present invention will be described with reference to drawings. FIG. 1 is a schematic diagram illustrating the configuration of a medical information system to which a clinical information processing apparatus according to an embodiment of the present invention has been applied. FIG. 2 is a functional block diagram of the clinical information processing apparatus according to the first embodiment. In the present embodiment, a case in which a clinical information processing apparatus 1 of the present invention is connected to information systems HIS 2, RIS 3, and the like through a network, as illustrated in FIG. 1, will be described. In these information systems, a HIS terminal 22, a RIS terminal 32, and a report terminal 33 are distributed for buildings, areas, or business sections within each hospital. These terminals are connected to each other through a network 36. Further, it is assumed that a modality 34 for imaging patients and a DICOM server 31 for storing patients' images are provided in the RIS 3, and that a storage server 21 for electronic charts (electronic medical charts) 200 is provided in the HIS 2.

For example, when reception data are input at the HIS terminal 22, the data are registered in an electronic chart 200 in the storage server 21, and the content of examination in each clinical department and a result of medical examination (test) are recorded in the electronic chart 200. Further, order information is input at the RIS terminal 32, and the RIS terminal 32 instructs each modality 34 to perform imaging based on the order information. A medical image 300 obtained by imaging is sent from each modality 34 to the DICOM server 31, and stored in the DICOM server 31.

The RIS terminal 32 has a function of retrieving a medical image 300 necessary for examination and diagnosis operations from the DICOM server 31, and a function of displaying the retrieved medical image 300. The report terminal 33 has a function of displaying a report on a medical examination and the condition of performed examination and treatment. If necessary, the RIS terminal 32 may instruct a CAD apparatus 35 to perform various kinds of image processing on an image stored in the DICOM server 31. Further, the result of image processing may be checked at the RIS terminal 32 and the report terminal 33. Further, information about a medical examination result and information about the condition of performed examination are stored also in the electronic chart 200.

The clinical information processing apparatus 1 according to the present embodiment includes a clinical information management server 10 and a clinical department terminal 11, which are connected to each other through a network. The clinical information management server 10 and the clinical department terminal 11 are controlled by a program installed from a recording medium, such as a CD-ROM, and function as the clinical information processing apparatus 1 of the present embodiment. The program may be installed after being downloaded from a storage device of a server connected through a network, such as the Internet.

The clinical information management server 10 includes a general-purpose computer 13 of relatively high processing power and a clinical information database 12. A software program providing a function of a database management system (DataBase Management System: DBMS) has been installed in the computer 13, and the clinical information database 12 is composed of a large capacity storage for storing registration case information, which will be described later. This storage may be a large capacity hard disk drive, or an NAS (Network Attached Storage) connected to a network, or a disk device connected to an SAN (Storage Area Network).

As illustrated in FIG. 2, the clinical information management server 10 includes a registration case information obtainment unit 101, a likelihood ratio information calculation unit 102, a weighting coefficient determination unit 103, a degree-of-similarity calculation unit 104, and a similar case output unit 105. The registration case information obtainment unit 101 obtains registration case information for calculating a likelihood ratio and registration case information for calculating a degree of similarity. The registration case information for calculating a likelihood ratio includes many registration cases correlated to plural items of clinical-information about plural comparison target patients, as clinical-information items each of which is classifiable into plural groups. The registration case information for calculating a degree of similarity includes many registration cases correlated to plural items of clinical-information about plural comparison target patients, as clinical-information items each of which is classifiable into plural groups. The likelihood ratio information calculation unit 102 calculates, based on the registration case information for calculating a likelihood ratio, likelihood ratio information for each classification of a key item that is one of plural clinical-information items correlated to the registration cases. In the likelihood ratio information, a likelihood ratio with respect to each classification of a clinical-information item or items of the plural clinical-information items other than the key item is correlated to each classification of the key item. With respect to each classification of the clinical-information item or items other than the key item, a likelihood ratio between a likelihood of belonging to one classification of the key item when a case belongs to each classification of the clinical-information item or items other than the key item and a likelihood of belonging to a different classification of the key item (any classification of the key item other than the one classification of the key item) when a case belongs to the respective classifications of the clinical-information item or items other than the key item is calculated. The weighting coefficient determination unit 103 determines weighting coefficient information in which a weighting coefficient corresponding to each classification of the clinical-information item or items other than the key item is correlated to each classification of the key item. The weighting coefficient determination unit 103 calculates, based on a target classification of a target clinical-information item and the likelihood ratio information, the weighting coefficient corresponding to each classification of the clinical-information item or items other than the key item for each classification of the key item. Accordingly, the weighting coefficient determination unit 103 determines weighting coefficient information in which each weighting coefficient corresponding to each classification of the clinical-information item or items other than the key item is correlated to each classification of the key item. The degree-of-similarity calculation unit 104 specifies, based on the determined weighting coefficient information, a weighting coefficient corresponding to each classification of the key item and each classification of the clinical-information item or items other than the key item for each of the registration cases included in the registration case information for calculating a degree of similarity. Further, the degree-of-similarity calculation unit 104 calculates a degree of similarity by using the specified weighting coefficients. The similar case output unit 105 detects a desirable registration case in the clinical information database 12 by a request from each terminal connected through a network. The desirable registration case is detected based on the calculated degree of similarity, and output to an origin of the request.

In the first embodiment described in the specification of the present invention, the registration case information for calculating a likelihood ratio and the registration case information for calculating a degree of similarity are exactly the same. Alternatively, the registration case information for calculating a likelihood ratio and the registration case information for calculating a degree of similarity may be different from each other, or overlap each other.

The clinical department terminal 11 is a computer used by a doctor in a clinical department to observe an image in detail, and to retrieve an image interpretation report, and to retrieve data from and input data into an electronic chart, and the like. The clinical department terminal 11 has a known hardware configuration including a CPU, a main storage device, an auxiliary storage device, an input output interface, a communication interface, an input device, a display device, a data bus, and the like. Further, a known operation system or the like has been installed in the clinical department terminal 11. The clinical department terminal 11 includes a general purpose processing apparatus (computer) 115, one or two high definition displays 113, and an input device 114, such as a keyboard and a mouse.

The processing apparatus 115 in the clinical department terminal 11 includes a target case obtainment unit 112 and a display control unit 111. The target case obtainment unit 112 obtains a classification of each of plural clinical-information items about a target patient input from the input device 114, such as a keyboard, as a target classification of each target clinical-information item. The display control unit 111 makes a display 113 display the registration case output from the similar case output unit 105, and the like. The display 113 displays information sent from each device connected through a network in a manner appropriate for each information. Further, software for assisting a doctor or the like who operates the clinical department terminal 11 is installed in the clinical department terminal 11. An operation, such as retrieval and registration of each clinical information, is performed by execution of a software program for each processing.

FIG. 3 is a diagram illustrating registration cases. FIGS. 4 and 5 are flow charts illustrating clinical information processing in the present embodiment. In FIGS. 4 and 5, steps are divided into steps before obtainment of a clinical-information item about a target patient and steps after obtainment the clinical-information item about the target patient. FIG. 5 illustrates steps in and after obtainment of a clinical-information item about the target patient. Steps illustrated in FIG. 4 are performed in arbitrary timing based on user's setting without regard to whether a clinical-information item about the target patient is obtained or not.

In each registration case used in degree-of-similarity calculation processing, likelihood ratio calculation processing and key item estimation processing, which will be described later, clinical-information items about comparison target patients are registered for each disease. As illustrated in FIG. 3, in the present embodiment, a diagnosed disease name, an age, fever, the grade of cough, the grade of sputum (sputum expectoration), and the number of white blood cells (WBC) are registered as the clinical-information items. The clinical-information items are, for example, patient's basic information, chief complaint, life history, an anamnesis, family history, various kinds of examination result data, various findings based on images, feature values of images, the content of performed treatment, genetic information, and the like.

The clinical information management server 10 in the present embodiment retrieves and obtains a case stored in each database connected through a network, and in which an electronic chart or a report has been generated. Further, the clinical information management server 10 newly registers the obtained case, as a registration case, and performs likelihood ratio information calculation processing and weighting coefficient calculation processing based on these kinds of registration case information. It is assumed that case obtainment processing, likelihood ratio information calculation, processing and weighting coefficient calculation processing have been set to be performed regularly at predetermined time. Alternatively, these kinds of processing may be performed at arbitrary timing based on a case addition request from each terminal.

First, the clinical information management server 10 obtains an unregistered case, as a registration case to be newly registered, from an electronic chart or the like stored in each database. Further, the clinical information management server 10 extracts a clinical-information item or items of the case, and reads data into a memory of the clinical information management server 10 (step ST01). When a diagnosis disease name is not present in the extracted clinical-information item or items (step ST02 is NO), the clinical information management server 10 adds the unregistered case, as a new registration case, in a clinical information database in such a manner to be correlated to the extracted clinical-information item or items (step ST06).

In contrast, when a diagnosis disease name is present in the extracted clinical-information item or items (step ST02 is YES), the registration case information obtainment unit 101 obtains, as registration cases, both of the new case correlated to the extracted clinical-information item or items and the registration case stored in the clinical information database 12 (step ST03).

Next, the likelihood ratio information calculation unit 102 generates frequency information based on the registration case information for calculating a likelihood ratio (step ST04). FIG. 6 is a diagram illustrating an example of frequency information. The frequency information classifies each clinical-information item of each registration case into groups. Further, the frequency information includes the total number of registration cases including the key item, which is one of clinical-information items, and the number of cases belonging to each classification of the key item. Here, disease names are used as the classification of the key item.

As illustrated in FIG. 6, the frequency information includes the calculated total number of registration cases belonging to each classification of the plural clinical-information items (age, fever (body temperature), cough, sputum, and white blood cell number) and the calculated number of a registration case or cases belonging to each classification of the plural clinical-information items for each disease name of registration cases. For example, in FIG. 6, the total number of registration cases in which fever is lower than 37 degrees is 24, and two cases of the 24 cases belong to a diagnosed disease name of pneumococcal pneumonia. Further, the total number of registration cases in which fever is higher than or equal to 37 degrees and lower than 38 degrees is 38, and one case of the 38 cases belongs to a diagnosed disease name of pneumococcal pneumonia. Further, the total number of registration cases in which fever is higher than or equal to 38 degrees is 67, and 13 cases of the 67 cases belong to a diagnosed disease name of pneumococcal pneumonia.

Classification of a clinical-information item classifies the clinical-information item into groups based on the type of the clinical-information item and a range of values representing the clinical-information item. The classification may be determined by a doctor or the like in an arbitrary manner based on a medical judgment standard. Here, the age is divided into three groups based on various medical diagnosis criteria, such as an average incidence of a disease corresponding to an age. Here, the three groups are an age group of younger than 40 years old, an age group of older than or equal to 40 years old and younger than 65 years old, and an age group of older than or equal to 65 years old. Further, each of fever (body temperature), cough, sputum, and white blood cell number is divided into a normal range and an abnormal range based on medical criteria obtained from clinical data or the like. Further, each of the abnormal ranges is divided into two grades based on the degree of abnormality. Therefore, each item is divided into three grades in total. The clinical-information item may be classified into arbitrary grades based on a demand in actual medical practice.

Then, the likelihood ratio information calculation unit 102 calculates, with respect to each classification of each clinical-information item, a likelihood ratio that is [a probability that a disease name is disease X]/[a probability that a disease name was not disease X] (step ST05). Calculation of the likelihood ratio is repeated for all disease names included in disease frequency information.

Here, each clinical-information item may be assumed to be independent from each other, and the likelihood ratio may be calculated based on Bayes theorem. According to Bayes theorem, if each clinical-information (A, B, C . . . ) is independent from each other, it is possible to represent probability P (X|A, B, C, . . . ) that a disease name after determination of clinical-information is disease X with respect to probability P(X) that a disease name before determination of the clinical-information (A, B, C . . . ) is disease X by the following formula (1). Similarly, it is possible to represent probability P(~X|A, B, C, . . . ) that a disease name is not disease X by the following formula (2).

$$P(X|A,B,C, \ldots )=P(A|X)*P(B|X)*P(C|X) \ldots *P(X)/P(A,B,C, \ldots ) \quad (1)$$

$$P(\sim X|A,B,C, \ldots )=P(A|\sim X)*P(B|\sim X)*P(C|\sim X) \ldots *P(\sim X)/P(A,B,C, \ldots ) \quad (2)$$

Likelihood ratio $LR(\alpha)$ of each classification $\alpha$ of a clinical-information item is defined by the following formula (3):

$$LR(\alpha)=P(\alpha|X)/P(\alpha|\sim X) \quad (3).$$

It is possible define the following formula (4) by using the formulas (1) and (2):

$$P(X|A,B,C,\ldots)/P(\sim X|A,B,C,\ldots) = LR(A)*LR(B)*LR(C)*\ldots*P(X)/P(\sim X) \quad (4).$$

Specifically, as formula (4) shows, it is possible to represent the degree of probability that a disease name is disease X by the product of likelihood ratios LR(A), LR(B), LR(C), . . . of the clinical-information items, respectively.

FIG. 7 is a diagram illustrating an example of likelihood ratio information calculated based on the frequency information in FIG. 6. For example, when a disease name is pneumococcal pneumonia, and fever that is a clinical-information item is classified into fever of higher than or equal to 38 degrees, the likelihood ratio is calculated in the following manner:

[a probability that a disease name is pneumococcal pneumonia when fever is higher than or equal to 38 degrees]

=[the number of cases in which a disease name is pneumococcal pneumonia when fever is higher than or equal to 38 degrees]/[the number of cases in which a disease name is pneumococcal pneumonia]

=13/(2+1+13)=0.81;

[a probability that a disease name is other than pneumococcal pneumonia when fever is higher than or equal to 38 degrees]

=[the number of cases in which a disease name is other than pneumococcal pneumonia when fever is higher than or equal to 38 degrees]/[the number of cases in which a disease name is other than pneumococcal pneumonia]

=(67−13)/((24+38+67)−(2+1+13))

=0.48; and

Likelihood ratio=[a probability that a disease name is pneumococcal pneumonia when fever is higher than or equal to 38 degrees]/[a probability that a disease name is other than pneumococcal pneumonia when fever is higher than or equal to 38 degrees]

=0.81/0.48

=1.69.

In the above example, the [number of cases in which a disease name is other than pneumococcal pneumonia when fever is higher than or equal to 38 degrees] is calculated by subtracting the number (13) of cases in which a disease name is pneumococcal pneumonia when the fever is higher than or equal to 38 degrees from the total number (67) of cases in which fever is higher than or equal to 38 degrees. Further, the [number of cases in which a disease name is other than pneumococcal pneumonia] is calculated by subtracting the number (2+1+13) of cases in which a disease name is pneumococcal pneumonia from the total number (24+38+67) of cases.

After then, the clinical information management server 10 adds a new case, as a registration case, in a registration case database (step ST06).

The present invention is not limited to the present embodiment. Registration case addition processing in step ST06 may be performed before steps ST02 through ST05.

When processing in steps ST01 through ST06 are regularly performed as described above, it is possible to update likelihood ratio information in such a manner to take a new case into consideration. Therefore, it is possible to calculate a weighting coefficient, which is determined based on the likelihood ratio information, in such a manner to take the new case into consideration. Further, it is possible to accurately calculate a degree of similarity. Since it is possible to automatically add registration cases, it is possible to reduce the work of updating registration cases, and that is efficient.

Next, with reference to FIG. 5, processing from obtainment of a clinical-information item of a target patient through extraction and display of a similar case by using the clinical information processing method of the present embodiment will be described. The similar case is a case, the clinical-information item of which is similar to that of the target patient.

Here, a case in which a doctor in a clinical department extracts, based on a target case of a target patient to be treated or diagnosed, a similar case of a comparison target patient by using a clinical department terminal 11 will be described. The extracted similar case is used for diagnosis.

First, the target case obtainment unit 112 receives an input by a user by the input device 114, and obtains a clinical-information item of the target patient (step ST11). Here, it is assumed that information including age: 50 years old, fever (body temperature): 38.9 degrees, cough: high grade, sputum: high grade, and white blood cell number: 8000 is obtained, as information about a target case, which is a case of a target patient. Further, a classification of each target clinical-information item is obtained as a target classification of each target clinical-information item.

Further, the weighting coefficient determination unit 103 determines weighting coefficients for each classification of the key item with respect to each classification of clinical-information item or items other than the key item. The weighting coefficient determination unit 103 determines each weighting coefficient, based on the target classification of each target clinical-information item and the likelihood ratio information, in such a manner that the weighting coefficient becomes larger as the likelihood ratio is higher (step ST12). The weighting coefficient determination unit 103 determines weighting coefficient information in which weighting coefficients corresponding to respective classifications of the clinical-information item or items other than the key item are correlated to each classification of the key item. FIG. 8 is a diagram illustrating an example of weighting coefficient information. The weighting coefficient determination unit 103 determines weighting coefficients by using different weighting methods to determine a weighting coefficient corresponding to a target classification and to determine a weighting coefficient corresponding to a classification other than the target classification. The different weighting methods are used to determine the weighting coefficients with respect to each clinical-information item or items so that weighting coefficients corresponding to classifications other than the target classification are not relatively large, compared with the weighting coefficient corresponding to the target classification. The weighting coefficients are determined in such a manner to evaluate a case in which a clinical-information item belongs to a target classification, as a case more similar to a target case than a case in which a clinical-information item belongs to any classification other than the target classification.

The weighting coefficient determination unit 103 determines, as a final weighting coefficient, a value based on the following criteria 1) through 3).

Criterion 1)

When the classification of a clinical-information item in a target case and the classification of the clinical-information item in a registration case are the same, and a likelihood ratio is greater than or equal to 1 (first threshold value), a weighting coefficient is increased based on the likelihood ratio.

Criterion 2)

When the classification of a clinical-information item in a target case and the classification of the clinical-information item in a registration case are the same, and a likelihood ratio is less than 1 (second threshold value), it is judged that the classification of the clinical-information item and the classification of the key item are substantially not related to each other. Therefore, weighting is performed in such a manner to lower the weighting coefficient. For example, a small value, such as 0, is used as the weighting coefficient.

Criterion 3)

When the classification of a clinical-information item in a target case and the classification of the clinical-information item in a registration case are not the same, weighting is performed based on the lower one of a likelihood ratio correlated to a target classification of each target clinical-information item and a likelihood ratio correlated to a classification of a clinical-information item of a registration case. When the lower likelihood ratio is greater than or equal to 1 (third threshold value), it is judged that the classification of the clinical-information item and the classification of the key item are related to each other to some extent. Therefore, the weighting coefficient is increased based on the likelihood ratio. When the lower likelihood ratio is less than 1 (fourth threshold value), it is judged that the classification of the clinical-information item and the classification of the key item are not related to each other. Therefore, weighting is performed in such a manner that the weighting coefficient is lower, as the likelihood ratio is lower. For example, the weighting coefficient is set at a small value, such as a negative value.

With respect to criterion 1), for example, when a likelihood ratio of belonging to specific disease Y (classification of the key item) is high if the classification of a clinical-information item is classification Z, the likelihood ratio indicates that a probability of belonging to disease Y is high if the classification of the clinical-information item is the classification Z (classification Y of the key item and the classification of the clinical-information item are closely related to each other). Therefore, weighting is performed in such a manner that the weighting coefficient becomes larger based on a likelihood ratio. Accordingly, with respect to a classification of a clinical-information item closely related to the classification Y of the key item, it is possible to increase an influence of the classification on calculation of a degree of similarity. In contrast, with respect to a classification of a clinical-information item that is slightly related to the classification Y of the key item, it is possible to reduce an influence of the classification on calculation of a degree of similarity. Therefore, it is possible to prevent the classification of the clinical-information item that is slightly related to the classification of the key item from influencing calculation of the degree of similarity more than necessarily. Hence, it is possible to accurately calculate the degree of similarity. Further, when the likelihood ratio is higher than or equal to 1 (first threshold value), it is estimated that the classification of the clinical-information item and the classification of the key item are closely related to each other. Therefore, the weighting coefficient is determined in such a manner that the weighting coefficient becomes larger as the likelihood ratio is higher. Hence, it is possible to determine the weighting coefficient in such a manner that classification of the clinical-information item that is slightly related to the classification Y of the key item is further differentiated from the classification Z of the clinical-information item that is recognized to be closely related to the classification Y of the key item. In other words, it is possible to judge a registration case having a classification of a clinical-information item that is recognized to be closely related to classification (disease name X) of the key item, as a case having a high likelihood of belonging to the disease name X, and to increase a degree of similarity of the registration case.

With respect to criterion 2), when a likelihood ratio is less than a predetermined value (second threshold value), it is estimated that the classification of the clinical-information item and the classification of the key item are not substantially related to each other. Therefore, weighting is performed in such a manner that the weighting coefficient becomes even smaller. Since the weighting coefficient corresponding to the classification of the clinical-information item that is slightly related to the classification (disease name) of the key item is further reduced, it is possible to determine the weighting coefficient in such a manner that classification of the clinical-information item slightly related to the classification (disease name) of the key item is further differentiated from the classification of the clinical-information item that is recognized to be closely related to the classification (disease name) of the key item.

With respect to criterion 3), when the classification of a clinical-information item in a target case and the classification of the clinical-information item in a registration case are not the same, a weighting coefficient is determined by using the lower one of a likelihood ratio correlated to a target classification of each target clinical-information item and a likelihood ratio correlated to a classification of a clinical-information item of a registration case. Conventionally, the degree of weighting is increased only when the classification of a clinical-information item is the same (values are close) as the target classification. However, unlike the conventional techniques, criterion 3) is based on an idea that even if a classification of the same clinical-information item is different from the target classification, if the effect of a probability of belonging to the classification of the key item (likelihood ratio) of the classification that is different from the target classification is similar to that of the target classification, the different classification of the clinical-information item and the target classification are related to the classification of the key item medically at a similar degree. For example, in the example of mycoplasma illustrated in FIG. 7, both of a likelihood ratio corresponding to WBC of less than 7900 and a likelihood ratio corresponding to WBC of greater than or equal to 7900 and less than 12000 are 1.4, and they are similar to each other. A probability of belonging to mycoplasma is substantially the same for WBC of less than 7900 and WBC of greater than or equal to 7900 and less than 12000. Therefore, it is not necessary to differentiate the two groups of WBC values from each other. Hence, weighting coefficients are determined by evaluating that both of a case of belonging to WBC of less than 7900 and a case of belonging to WBC of greater than or equal to 7900 and less than 12000 have the same degree of probability of belonging to mycoplasma. Here, the lower one of the likelihood ratio of the target classification and the likelihood ratio of a classification other than the target classification of the same clinical information item is used. The lower likelihood ratio is used to determine the weighting coefficient in such a manner that the weighting coefficient corresponding to the classification other than the target classification is not relatively larger than the weighting coefficient of the target classification.

Specifically, weighting is performed based on criteria 1) through 3) in the following manner:

(i) When a target classification of each target clinical-information item and a classification of a clinical information item are the same and a likelihood ratio is greater than or equal to 1, a logarithm of the likelihood ratio is used as the weighting coefficient.

(ii) When a target classification of each target clinical-information item and a classification of a clinical information item are the same and a likelihood ratio is less than 1, 0 is used as the weighting coefficient.

(iii) When a target classification of each target clinical-information item and a classification of a clinical information item are not the same, a logarithm of the lower one of the likelihood ratio corresponding to the classification of the clinical-information item coinciding with the target classification of each target clinical-information item and the likelihood ratio corresponding to a classification of a clinical-information item that does not coincide with the target classification of each target clinical-information item is used as the weighting coefficient.

Here, as described in the aforementioned sections (i) and (iii), the weighting coefficient is calculated by using a value obtained by applying logarithm transformation to the likelihood ratio corresponding to each clinical-information item. The weighting coefficient is calculated in such a manner, because it is possible to use the effect of data of ratios, as the effect of all of the clinical-information items, by addition and subtraction. The sum of values that have been obtained by applying logarithm transformation to the likelihood ratio of each classification of the clinical-information item is the same as a value obtained by applying logarithm transformation to the product value of the likelihood ratio of each classification of the clinical-information item. Therefore, a value obtained by applying logarithm transformation to the likelihood ratio of each classification of the clinical-information item is determined, as the weighting coefficient. Further, the total of the weighting coefficient of each classification of the clinical-information item is used to evaluate a degree of similarity. Accordingly, it is possible to make the product of the likelihood ratio of each classification of the clinical-information item reflected in evaluation of the degree of similarity. As formula (4) shows, a probability of belonging to the key item (disease X) is a function of the product value of the likelihood ratio of each clinical-information item. Therefore, it is possible to make the probability of belonging to the key item appropriately reflected in the degree of similarity by calculating the degree of similarity by using the sum of values that have been obtained by applying logarithm transformation to the likelihood ratio of each clinical-information item, and to accurately evaluate the degree of similarity.

The present invention is not limited to the present embodiment. The weighting coefficient determination unit 103 may determine the weighting coefficient by using various methods as long as the weighting coefficient is determined, based on the likelihood ratio information, in such a manner that the degree of weighting is higher as the likelihood ratio is higher. For example, the value of the likelihood ratio may be directly used as the weighting coefficient.

With respect to the aforementioned section (ii), when the likelihood ratio is less than or equal to 1, a probability of belonging to a classification (disease name) of a key item when a case belongs to the classification of the registration case corresponding to the likelihood ratio is low. Therefore, the weighting coefficient is 0. Weighting may be performed, for example, in such a manner that the weighting coefficient becomes negative (the absolute value of the negative value is larger) as long as the weighting coefficient is determined in such a manner that the degree of weighting becomes lower when the likelihood ratio is less than or equal to 1. When the likelihood ratio is less than or equal to 1, it is estimated that the classification of the clinical-information item and the classification of the key item are substantially not related to each other. In this case, it is possible to determine the weighting coefficients in such a manner to further differentiate the classification of the clinical-information item that is slightly related to the classification (disease name) of the key item from the classification of the clinical-information item that is closely related to the classification (disease name) of the key item.

With respect to the aforementioned section (iii), weighting may be performed in such a manner that the weighting coefficient corresponding to a classification other than the target classification of each target clinical-information item becomes a negative value when one of the likelihood ratio corresponding to the target classification of the clinical-information item in the target case and the likelihood ratio corresponding to the classification other than the target classification of the clinical-information item is less than 1 (fourth threshold value). In this case, it is possible to determine the weighting coefficients in such a manner to further differentiate the classification of the clinical-information item that is slightly related to the classification (disease name) of the key item from the classification of the clinical-information item that is closely related to the classification (disease name) of the key item.

Arbitrary numerical values may be set as the first threshold value and the third threshold value based on the value of the likelihood ratio as long as the numerical values can evaluate that the classification of the clinical-information item is substantially closely related to the classification of the key item (a probability of belonging to the classification of the key item when a case belongs to the classification of the clinical-information item). It is desirable that the first threshold value and the third threshold value are greater than or equal to 1 and less than or equal to 2. For example, it is appropriate that the first threshold value and the third threshold value are 1. The first threshold value and the third threshold value may be the same value, or different values from each other.

Arbitrary numerical values may be set as the second threshold value and the fourth threshold value based on the value of the likelihood ratio as long as the numerical values can evaluate that the classification of the clinical-information item is substantially slightly related to the classification of the key item (a probability of belonging to the classification of the key item when a case belongs to the classification of the clinical-information item). It is desirable that the second threshold value and the fourth threshold value are greater than or equal to 0.5 and less than or equal to 1. The second threshold value is less than or equal to the first threshold value, and the fourth threshold value is less than or equal to the third threshold value. For example, it is appropriate that the second threshold value and the fourth threshold value are 1. The second threshold value and the fourth threshold value may be the same value, or different values from each other.

The weighting coefficient determination unit 103 may adopt an arbitrary weighting method as long as weighting is further performed in such a manner that the weighting coefficient in the weighting coefficient information corresponding to the target classification of each target clinical-information item, and which is correlated to each classification of the key item, is relatively larger than the weighting coefficient in the weighting coefficient information corresponding to each classification of each clinical-information item other than the target classification of each target clinical-information item, and which is correlated to each classification of the key item. For example, weighting may be performed in such a manner that the degree of weighting on the classification of the clinical-information item coinciding with the target classification of the clinical-information item in the target case is higher. Further, weighting may be performed, based on the degree of non-coincidence between the target classification of the clinical-information item in the target case and the classification of the clinical-information item of a registration case, in such a manner that the degree of weighting on the classification of the clinical-information item of the registration case that does not coincide with the target classification of the clinical-information item of the target case becomes lower as the degree of non-coincidence is higher.

In the example of the degree-of-similarity determination information illustrated in FIG. 8, first, logarithm transformation is applied to each likelihood in the likelihood ratio information illustrated in FIG. 7 for example. In FIG. 8, the target classification of the target information is indicated by a bold line frame. For example, the age in the clinical-information item of the target case is 50 years old. Therefore, the target classification of the clinical-information item is an age of older than or equal to 40 years old and younger than 65 years old.

Further, with respect to a classification belonging to the target classification (bold line frame part) in the clinical-information item of the target case, and in which the likelihood ratio is greater than or equal to 1, a value obtained by applying logarithm transformation to the likelihood ratio is directly determined as the weighting coefficient based on section (i). Further, based on section (ii), with respect to a classification belonging to the target classification (bold line frame part) in each target clinical-information item, and in which the likelihood ratio is less than 1, 0 is determined as the weighting coefficient. For example, among each likelihood ratio corresponding to the age of older than or equal to 40 years old and younger than 65 years old, likelihood ratios corresponding to mycoplasma, pulmonary tuberculosis, and diffuse panbronchiolitis are 0.7, 0.6, and 0.8, which are less than 1, respectively. Therefore, weighting coefficients corresponding to mycoplasma, pulmonary tuberculosis, and diffuse panbronchiolitis are 0. Further, based on section (iii), when the target classification of each target clinical-information item and the classification of the clinical-information item do not coincide with each other (a part other than the bold line frame part), a logarithm value of the lower one of the likelihood ratio corresponding to the classification of the clinical-information item coinciding with the target classification of each target clinical-information item and the likelihood ratio corresponding to the classification of the clinical-information item that does not coincide with the target classification of each target clinical-information item is determined as the weighting coefficient. For example, when the weighting coefficient of the classification of age of older than or equal to 65 years old, which does not coincide with the target classification, is to be determined, likelihood ratios corresponding to pneumococcal pneumonia are compared. Specifically, the likelihood ratio corresponding to age of older than or equal to 65 years old, which does not coincide with the target classification, is 1.7, and the likelihood ratio corresponding to age of older than or equal to 40 years old and younger than 65 years, which coincides with the target classification, is 1.2, and these likelihood ratios are compared with each other. Further, a logarithm value of 1.2 that is the lower one of the likelihood ratios is 0.2, and 0.2 is determined as the weighting coefficient corresponding to the disease name of pneumococcal pneumonia and the classification of age of older than or equal to 65 years old.

When the weighting coefficient is calculated based on the likelihood ratio as described above, both of "a probability of belonging to a specific classification of a key item when a clinical-information item belongs to a specific classification (in the above example, fever is higher than or equal to 38 degrees and the disease name is pneumococcal pneumonia)" (P (A|X) in formula (3)), and "a probability of belonging to a classification other than the specific classification of a key item when a clinical-information item belongs to the specific classification (in the above example, fever is higher than or equal to 38 degrees and the disease name is different from pneumococcal pneumonia)" (P(A|~X) in formula (3)) are used. Therefore, it is possible to determine the weighting coefficient in such a manner that the probability is more accurately reflected with respect to each classification of the key item, compared with the case of determining the weighting coefficient only based on the "probability of belonging to a specific classification of a key item when a clinical-information item belongs to a specific classification" (P(A|X) in formula (3)).

In the aforementioned likelihood ratio calculation processing and the aforementioned weighting information calculation processing, when the number of registration cases in a classification of the key item is extremely small, it is desirable that the numerical value representing the frequency or the likelihood ratio of each classification of each clinical-information item correlated to the classification of the key item is corrected.

Next, the degree-of-similarity calculation unit 104 obtains the registration case information in a storage means, such as a memory (step ST13). When a registration case in which a degree of similarity has not been calculated is present (step ST14 is YES), the degree-of-similarity calculation unit 104 obtains the weighting coefficient corresponding to a value representing the clinical-information item in each registration case from the weighting coefficient information illustrated in FIG. 8. Further, with respect to the clinical-information item of the registration case, the degree-of-similarity calculation unit 104 extracts the weighting coefficient corresponding to each classification (disease name) of a key item of the registration case and the classification of a clinical-information item other than the key item, and calculates the degree-of-similarity determination information. FIG. 9 is a diagram illustrating an example of degree-of-similarity determination information calculated based on the registration case information illustrated in FIG. 3 and the weighting information illustrated in FIG. 8. With respect to the registration case, extracted weighting coefficients are accumulated, and the cumulative value is calculated as the degree of similarity between the registration case and the case of the target patient (step ST15).

With reference to FIGS. 3, 8 and 9, a method for calculating a degree of similarity will be described by using case 1 in FIG. 3, as a specific example. As FIG. 3 illustrates, in case 1, the disease name is pneumococcal pneumonia, and age is 62 years old. The degree-of-similarity calculation unit 104 determines, based on the weighting coefficient table illustrated in FIG. 8, the weighting coefficient corresponding to this disease name and this age, as 0.2, which is correlated to the disease name of pneumococcal pneumonia, and age of older than or equal to 40 year old and younger than 65 years old. Similarly, the degree-of-similarity calculation unit 104 extracts the weighting coefficient corresponding to the disease name of the registration case and each classification of each clinical-information item other than the disease name for each clinical information item. Accordingly, the degree-of-similarity calculation unit 104 calculates degree-of-similarity determination information, as illustrated in FIG. 9.

As illustrated in FIG. 9, the weighting coefficients determined for age, fever (body temperature), cough, sputum and WBC, which are clinical-information items of case 1, are accumulated. The weighting coefficients determined for age, fever (body temperature), cough, sputum and WBC are 0.2, 0.5, −0.5, −0.5, and 0, respectively, and the cumulative value is −0.3 (=0.2+0.5+(−0.5)+(−0.5)+0). The cumulative value is determined as the degree of similarity.

When there is no registration case in which the degree of similarity has not been calculated (step ST14 is NO), registration cases are sorted in the order of degrees of similarity, and a list of similar cases is created (step ST16).

Further, the similar case output unit 105 extracts, from the list of similar cases, a case the calculated degree of similarity of which is higher than a predetermined value, as a similar case, which is similar to a target case of a target patient. Further, the similar case output unit 105 retrieves information related to the extracted similar case (similar case information) from a storage server 21, a DICOM server 31, or the like through the network. Further, the similar case output unit 105 outputs the retrieved similar case information to a clinical department terminal 11.

Figure 11:
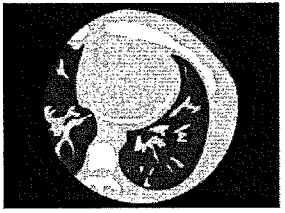
FIG. 11 is a diagram illustrating an example of display of a similar case extraction result in the first through third embodiments (detailed display)

The display control unit 111 provided in the clinical department terminal 11 displays the received similar case information on the display 113 in accordance with a set display option (step ST17). FIG. 10 is a diagram illustrating an example of display of a list of similar cases. FIG. 11 is a diagram illustrating an example of detailed display of a similar case. Here, the display control unit 111 displays the similar cases in the descending order of degrees of similarity. The display control unit 111 displays information about each similar case in accordance with the display option that has been set in advance in such a manner that the summary of each similar case is recognizable. Here, a degree of similarity, patient's basic information including the age and the sex of a patient, a disease name, the content of treatment (drug administration), a chief complaint summary representing a main symptom (here, a body temperature and the content of a chief complaint), an examination result, and a thumbnail of a diagnosis image are displayed for each similar case. This display option, such as display items, arrangement, and the order of arrangement of cases, may be set in an arbitrary manner based on a demand of a user. The display control unit 111 displays, based on the degrees of similarity, a list of registration cases in the descending order of degrees of similarity in such a manner that each registration case includes each value or type of a clinical-information item the likelihood ratio of which is higher than or equal to a predetermined value.

Further, as illustrated in FIG. 11, the display control unit 111 may display, in detail, a similar case that has been selected from the list of the similar cases by a user. For example, when the user selects a thumbnail in FIG. 10 at the input device 114, the display control unit 111 receives the selection, and displays detailed data of the similar case corresponding to the selected thumbnail on the display 113. Further, the display control unit 111 displays the detailed data in such a manner that a classification of a clinical-information item corresponding to a large weighting coefficient is identifiable. In the example illustrated in FIG. 11, cough, which is a clinical-information item the value of the weighting coefficient of which is large, is distinguishably displayed by using a double bold line frame. Further, fever and white blood cell number, which are clinical-information items the values of the weighting coefficients of which are slightly large, are distinguishably displayed by using bold line frames. Further, sputum, which is a clinical-information item the value of the weighting coefficient is small, is distinguishably displayed by displaying letters in gray.

In the aforementioned clinical information processing apparatus, a likelihood of belonging to one classification of a key item when a case belongs to each classification of a clinical-information item other than the key item included in the registration cases and a likelihood of belonging to any classification of a key item other than the one classification of the key item when a case belongs to each classification of a clinical-information item other than the key item included in the registration cases are calculated, based on the registration case information, for each classification of the key item correlated the registration cases. Further, a likelihood ratio between the likelihood of belonging to one classification of the key item and the likelihood of belonging to any classification of the key item other than the one classification is calculated with respect to each classification of the clinical-information item other than the key item. Further, a weighting coefficient is determined, based on likelihood ratio information, for each classification of the key item in such a manner that the weighting coefficient of the clinical-information item other than the key item is larger as the calculated likelihood ratio is higher. Therefore, if a small number of cases that are sufficient to judge the distribution of classifications of the clinical-information item are present, it is possible to determine the weighting coefficient. Even if the number of cases is relatively small, it is possible to accurately calculate the degree of similarity. Therefore, the present invention is widely adoptable even by a hospital or the like that has a relatively small number of past cases, and that is practical.

Further, it is possible to determine each weighting coefficient in such a manner to reflect not only a likelihood of belonging to one classification of a key item but also a likelihood of not belonging to the one classification of the key item. Therefore, even if the number of cases of comparison target patients is small, it is possible to more accurately determine the weighting coefficient, compared with the case of determining the weighting coefficient only based on the likelihood (probability) of belonging to one classification of the key item.

Further, each weighting coefficient is determined, based on a clinical-information item (key item), such as a disease name, which represents an important characteristic in diagnosis. Each weighting coefficient is determined for each classification of each clinical-information item in such a manner that the degree of weighting is higher as a likelihood representing a probability of belonging to a specific classification of the key item is higher. Therefore, it is possible to accurately calculate a degree of similarity between a case of a target patient and a registration case in such a manner that a characteristic corresponding to a classification of the key clinical-information item, such as a disease name, is appropriately reflected. In contrast, in Patent Document 1, it is impossible to calculate a degree of similarity by performing weighting based on the characteristic of a clinical-information item that a closely related symptom differs depending on a disease name. Further, in Patent Document 2, when a degree of influence is determined to perform weighting, the characteristic of a clinical-information item that a closely related classification of a clinical-information item differs depending on a disease name is not reflected. Therefore, it is impossible to determine the weighting coefficient in such a manner to appropriately reflect the characteristic of the clinical-information item.

Further, when a degree of similarity is calculated by simply using a probability, which tends to be influenced by the number of cases of each disease, the probability of a rare case becomes extremely low. Therefore, the rare case does not tend to be extracted as a similar case. However, since the likelihood represents a probability of belonging to each disease name (classification of a key item), the degree of similarity does not tend to be influenced by the number of cases. Therefore, even if a case is related to a disease name in which the number of cases is small, it is possible to extract the case as a similar case. Extraction of the similar case is not prevented by cases that are related to a different disease name including many cases.

According to the clinical information processing apparatus, it is possible to automatically determine an appropriate weighting coefficient. Therefore, even if a user is not used to diagnosis, it is possible to easily calculate a degree of similarity. In contrast, when the degree of weighting of a weighting coefficient is specified by a setting operation by a user, the setting operation is limited to a user, such as a doctor, who has special knowledge of medical diagnosis. Further, the setting operation is required.

Here, the method for calculating the degree of similarity is not limited to the aforementioned method for calculating a cumulative value of weighting coefficients, as the degree of similarity. Alternatively, a distance of a weighting coefficient of a clinical-information item of a registration case with respect to a clinical-information item of a target case may be calculated, as an index representing a degree of similarity. Then, a case in which the distance is short may be judged as a similar case.

The display control unit 111 displays a list of similar cases in the order of the degrees of similarity. Therefore, a user such as a doctor can refer to diagnosis data, such as a disease name of a case in which a clinical-information item is similar to that of a target patient and a detailed content of treatment, in the list of similar cases. Therefore, it is possible to efficiently and accurately estimate the disease name of a target patient, and to determine a treatment policy of the target patient.

The display control unit 111 displays a list of the registration cases, based on the calculated degrees of similarity, in such a manner that each registration case includes information about a classification of a clinical-information item in which a likelihood ratio or a weighting coefficient is greater than or equal to a predetermined value. Therefore, it is possible to easily recognize a classification of a clinical-information item closely related to a key item.

Further, the display control unit 111 displays, based on a weighting coefficient, in such a manner that a clinical-information item in which the degree of weighting is high is distinguishable. Therefore, a doctor or the like can easily recognize a part in which a similar case and a case of a target patient are similar to each other. Further, the display control unit 111 displays, based on a weighting coefficient, in such a manner that a clinical-information item in which the degree of weighting is low is distinguishable. Therefore, a doctor or the like can easily recognize a part in which a similar case and a case of a target patient are not similar to each other.

Further, the display control unit 111 can display detailed information about selected case information based on a selection operation by a user. Therefore, the work of the user is reduced. Further, it is possible to sufficiently extract information that is necessary for diagnosis, and to present the information to the user.

Figure 12:
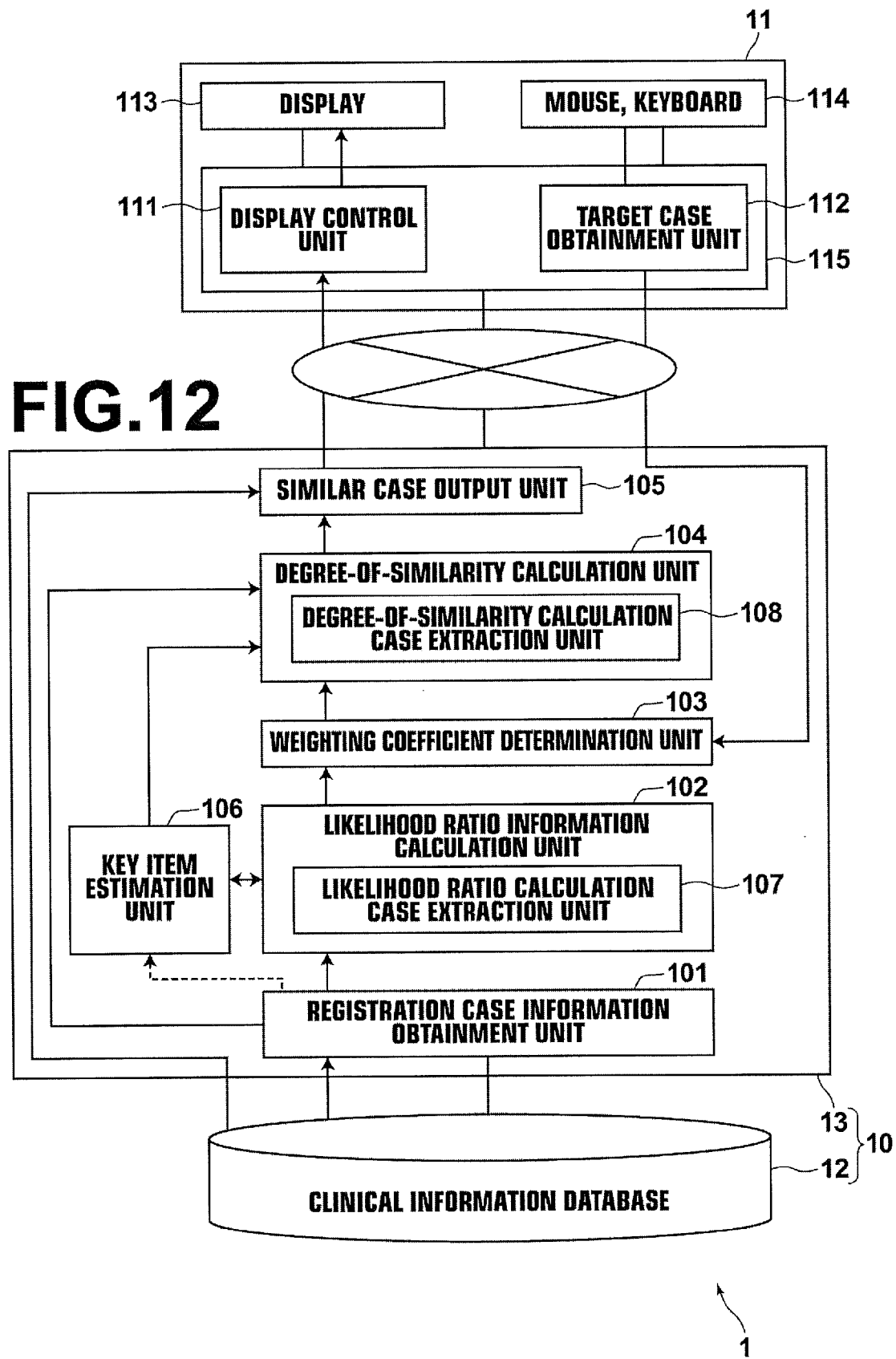
FIG. 12 is a functional block diagram of a clinical information processing apparatus according to the second embodiment.

Next, a second embodiment will be described. In the second embodiment, a function for limiting registration cases for calculating a likelihood ratio or a function for limiting registration cases for calculating a degree of similarity is provided in the clinical information processing apparatus of the first embodiment. FIG. 12 is a functional block diagram of the second embodiment.

As illustrated in FIG. 12, the clinical information processing apparatus 1 of the second embodiment differs from the first embodiment in the following points. In the second embodiment, the registration case information obtainment unit 101 further obtains registration cases for estimating a key item, and a key item estimation unit 106 is provided. The key item estimation unit 106 estimates, based on a case of a target patient, a classification (a disease name) of a key item of clinical-information items of the target patient. Further, the likelihood ratio information calculation unit 102 includes a likelihood ratio calculation case extraction unit 107, and calculates likelihood ratio information only based on an extracted registration case or cases for calculating a likelihood ratio. The likelihood ratio calculation case extraction unit 107 extracts, as a registration case or cases for calculating a likelihood ratio, only a registration case or cases that belong to the estimated classification of the key item. Further, the degree-of-similarity calculation unit 104 includes a degree-of-similarity calculation case extraction unit 108, and calculates a degree of similarity only based on the extracted registration case or cases for calculating a degree of similarity. The degree-of-similarity calculation case extraction unit 108 extracts, as a registration case or cases for calculating a degree of similarity, only a registration case or cases that belong to the estimated classification of the key item.

Figure 13:
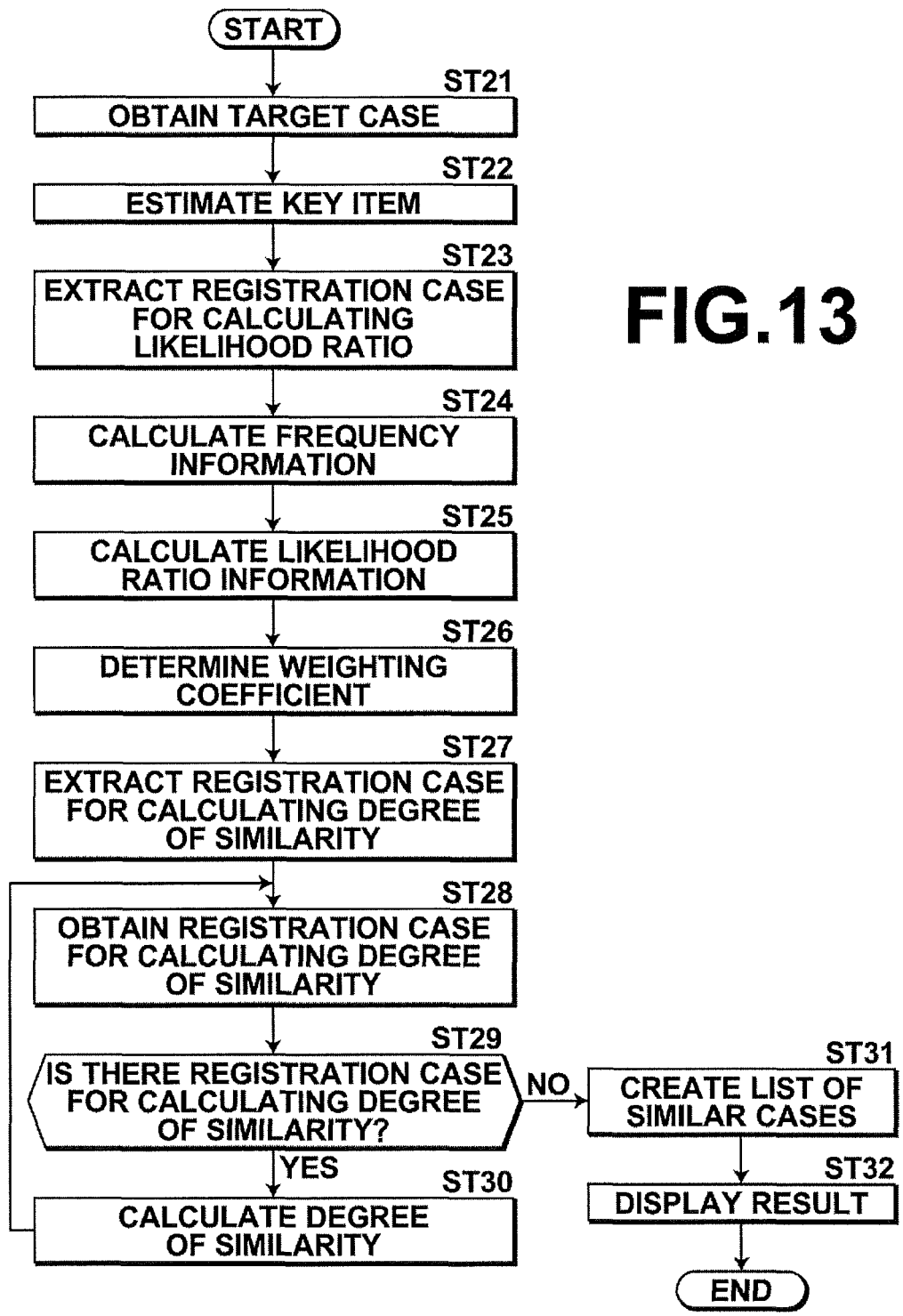
FIG. 13 is a flow chart illustrating a flow of clinical information processing in the second embodiment.

FIG. 13 is a flow chart for explaining a flow of processing in and after obtainment of a clinical-information item about a target patient in the second embodiment. In the second embodiment, steps ST01 through ST06, which are illustrated in FIG. 4, are the same as those of the first embodiment. Therefore, explanations of steps ST01 through ST06 will be omitted. With reference to the flow chart illustrated in FIG. 13, features different from the first embodiment will be mainly described, and the same features as the first embodiment will be omitted.

In FIG. 13, first, the target case obtainment unit 112 obtains a clinical-information item of a target patient in a similar manner to the first embodiment (step ST21).

Then, the key item estimation unit 106 calculates, based on the likelihood ratio information illustrated in FIG. 7, a product for each classification of the key item, and the product value is obtained by multiplying a likelihood ratio corresponding to a target classification of each target clinical-information item. When the calculated product value satisfies a predetermined condition, which will be described later, it is tentatively estimated that the target patient belongs to the classification of the key item (step ST22).

When Bayes theorem, as described above, is used, index LRX representing a probability that the key item of the target patient is classification X (the disease name is disease X) is obtained, as follows by using the formula (4):

$$LRX=LR(A)*LR(B)*LR(C)* \ldots \qquad (5).$$

In the present embodiment, likelihood ratio $LR(\alpha)$ corresponding to a target classification of each target clinical-information item is calculated, based on the frequency information illustrate in FIG. 6, for each classification of the key item. Further, the likelihood ratio is multiplied by using the formula (5) for each classification of the key item. Accordingly, probability LRX of belonging to each classification of the key item is calculated. Here, a likelihood ratio that a disease name is disease X is calculated for each target classification of each clinical-information item. Further, the calculated likelihood ratio is multiplied to calculate probability LRX that the disease name is disease X. Further, probability LRX is calculated for each of all disease names, and it is estimated that a disease name in which the probability LRX is the highest is the disease name of the target patient.

Specifically, a likelihood ratio of a target classification to which each target clinical-information item of a target patient belongs is extracted from the likelihood ratio information illustrated in FIG. 7, and key item estimation information is generated. FIG. 14 is a diagram illustrating an example of key item estimation information. For example, when a target case, which is a case of a target patient, is age: 50 years old, fever (body temperature): 38.9 degrees, cough: high grade, sputum: high grade, and white blood cell number: 8000, likelihood ratios are extracted for each disease name from the likelihood ratio information illustrated in FIG. 7. Specifically, a likelihood corresponding to age of older than or equal to 40 years old and younger than or equal to 65 years old, which is a classification of the clinical-information item to which the age (50 years old) of the target case belongs, is extracted. A likelihood corresponding to fever of 38 degrees or higher, which is a classification to which fever (38.9 degrees) of the target case belongs, is extracted. A likelihood corresponding to cough of high grade, which is a classification to which cough (high grade) of the target case belongs, is extracted. A likelihood corresponding to sputum of high grade, which is a classification to which sputum (high grade) of the target case belongs, is extracted. A likelihood corresponding to white blood cell number of higher than or equal to 7900 and less than 12000, which is a classification to which white blood cell number (8000) of the target case belongs, is extracted. Accordingly, the key item estimation information illustrated in FIG. 14 is generated. The key item estimation information illustrated in FIG. 14 is the same as information obtained by extracting only the bold line frame part from FIG. 7 and by correlating the extracted classification for each disease name.

Further, the key item estimation unit 106 multiplies the likelihood ratio corresponding to the classification of each clinical-information item correlated to each disease name. Accordingly, the key item estimation unit 106 calculates an overall likelihood ratio. In FIG. 14, for example, with respect to pneumococcal pneumonia, likelihood ratios of 1.2, 1.7, 0.6, 0.6, and 0.8 are correlated to age, fever, cough, sputum, and white blood cell number, which are clinical-information items, respectively. The overall likelihood ratio for pneumococcal pneumonia is a value obtained by multiplying all of the correlated likelihood ratios. The overall likelihood ratio is 0.59 (=1.2×1.7×0.6×0.6×0.8). In the example illustrated in FIG. 14, the key item estimation unit 106 tentatively estimates that a predetermined number of disease names in which the overall likelihood ratio is high are estimated disease names of the target patient. Here, the predetermined number of disease names are counted from a disease name in which the overall likelihood ratio is the highest. The predetermined number may be arbitrarily set by a user, such as a doctor, based on various conditions such as the number of registration cases. Further, the estimated key item may be estimated by using any kind of method as long as the classification of the key item of the target patient is estimated based on the overall likelihood ratio. For example, it may be estimated that a classification in which the overall likelihood ratio of the key item is higher than or equal to a predetermined value is a classification of the key item of the target patient.

Next, the likelihood ratio calculation case extraction unit 107 extracts, as registration cases for calculating a likelihood ratio, registration cases correlated to plural estimated disease names respectively (step ST23).

The likelihood ratio information calculation unit 102 calculates frequency information by using the same method as steps ST03 and ST04 illustrated in FIG. 4. Here, only the registration cases for calculating a likelihood ratio are a target of calculation. Further, the likelihood ratio information calculation unit 102 stores the calculated frequency information (step ST24). Next, the likelihood ratio information calculation unit 102 calculates likelihood ratio information based on the stored frequency information by using the same method as step ST05 illustrated in FIG. 4. Further, the likelihood ratio information calculation unit 102 stores the calculated likelihood ratio information (step ST25).

Further, the weighting coefficient determination unit 103 determines a weighting coefficient based on the calculated likelihood ratio information by using a similar method to the first embodiment (step ST26).

Next, the degree-of-similarity calculation case extraction unit 108 according to the second embodiment extracts, based on plural estimated disease names, only registration cases correlated to the plural estimated disease names respectively, as registration cases for calculating a degree of similarity, which are targets of calculation of a degree of similarity (step ST27). Further, the degree-of-similarity calculation unit 104 obtains only the extracted registration cases for calculating a degree of similarity (step ST28). If there is a registration case for calculating a degree of similarity in which a degree of similarity has not been calculated (step ST29 is YES), the degree-of-similarity calculation unit 104 performs degree-of-similarity calculation processing by using the same method as step ST15 illustrated in FIG. 4 (step ST30). In contrast, if there is no registration case for calculating a degree of similarity in which a degree of similarity has not been calculated (step ST29 is NO), the degree-of-similarity calculation unit 104 sorts the registration cases for calculating a degree of similarity in the order of degrees of similarity, and creates a list of similar cases (step ST31). Further, the degree-of-similarity calculation unit 104 displays the list of similar cases by using the same method as step ST17 illustrated in FIG. 4 (step ST32).

According the second embodiment, calculation of a degree of similarity is limited only to registration cases that satisfy a predetermined condition. Therefore, even if the number of registration cases is extremely large, it is possible to extract similar cases at high speed, while suppressing a load of calculation. Further, when a registration case that has been known to be clearly not similar to a target case is removed, it is possible to efficiently determine a degree of similarity at high speed without increasing a load of calculation more than necessarily.

Further, since the registration cases used to calculate a degree of similarity are limited based on the key item estimated from the target case, it is possible to effectively limit the target of calculation of a degree of similarity to registration cases in which a probability of being similar the target patient case is high. Further, it is possible to save the user's work of setting a condition for determining registration cases for calculating a degree of similarity.

Further, since calculation of a likelihood ratio is limited to registration cases that satisfy a predetermined condition, a case that is clearly not related is removed. Therefore, it is possible to prevent the frequency information and the weighting coefficient from being influenced by information about various many cases. Consequently, it is possible to prevent deterioration of accuracy in evaluation of weighting. For example, when the likelihood ratio information is calculated by limiting the target of calculation to registration cases correlated to a disease name, such as pneumonia, which has various types, it is possible to perform weighting in such a manner that a difference in the characteristic of each type of pneumonia is accurately reflected.

Further, since registration cases used to calculate a likelihood ratio are limited based on the key item estimated from the target case, it is possible to effectively limit the target of calculating a likelihood to registration cases in which a probability of being similar the target patient case is high. Further, it is possible to save the user's work of setting a condition for determining registration cases for calculating a likelihood ratio.

In the second embodiment, the likelihood ratio calculation case extraction unit 107 and the degree-of-similarity calculation case extraction unit 108 are not limited to the aforementioned examples. The predetermined condition for extracting the registration cases for calculating a likelihood ratio and the registration cases for calculating a degree of similarity may be set in an arbitrary manner based on a request from an actual diagnosis place, or the like. For example, the predetermined condition for extracting the registration cases for calculating a likelihood ratio and the registration cases for calculating a degree of similarity may be a condition that a registration case belongs to a disease name that has been set in advance by an input by a doctor, or the like. The predetermined condition for extracting the registration cases for calculating a degree of similarity may be a condition that at least one likelihood ratio corresponding to the classification of each clinical-information item is higher than or equal to a predetermined value (fifth threshold value) based on the likelihood ratio information. Alternatively, the predetermined condition for extracting the registration cases for calculating a degree of similarity may be a condition that a registration case is correlated to a likelihood ratio that is ranked higher than or equal to a predetermined rank among registration cases for calculating a degree of similarity based on the likelihood ratio information. In these cases, it is possible to limit the number of cases for calculating a degree of similarity. Therefore, it is possible to reduce a load of calculation in degree-of-similarity calculation processing, and to perform the degree-of-similarity calculation processing at higher speed.

In the clinical information processing apparatus 1 in the second embodiment, one of the likelihood ratio calculation case extraction unit 107 and the degree-of-similarity calculation case extraction unit 108 may be omitted.

Figure 15:
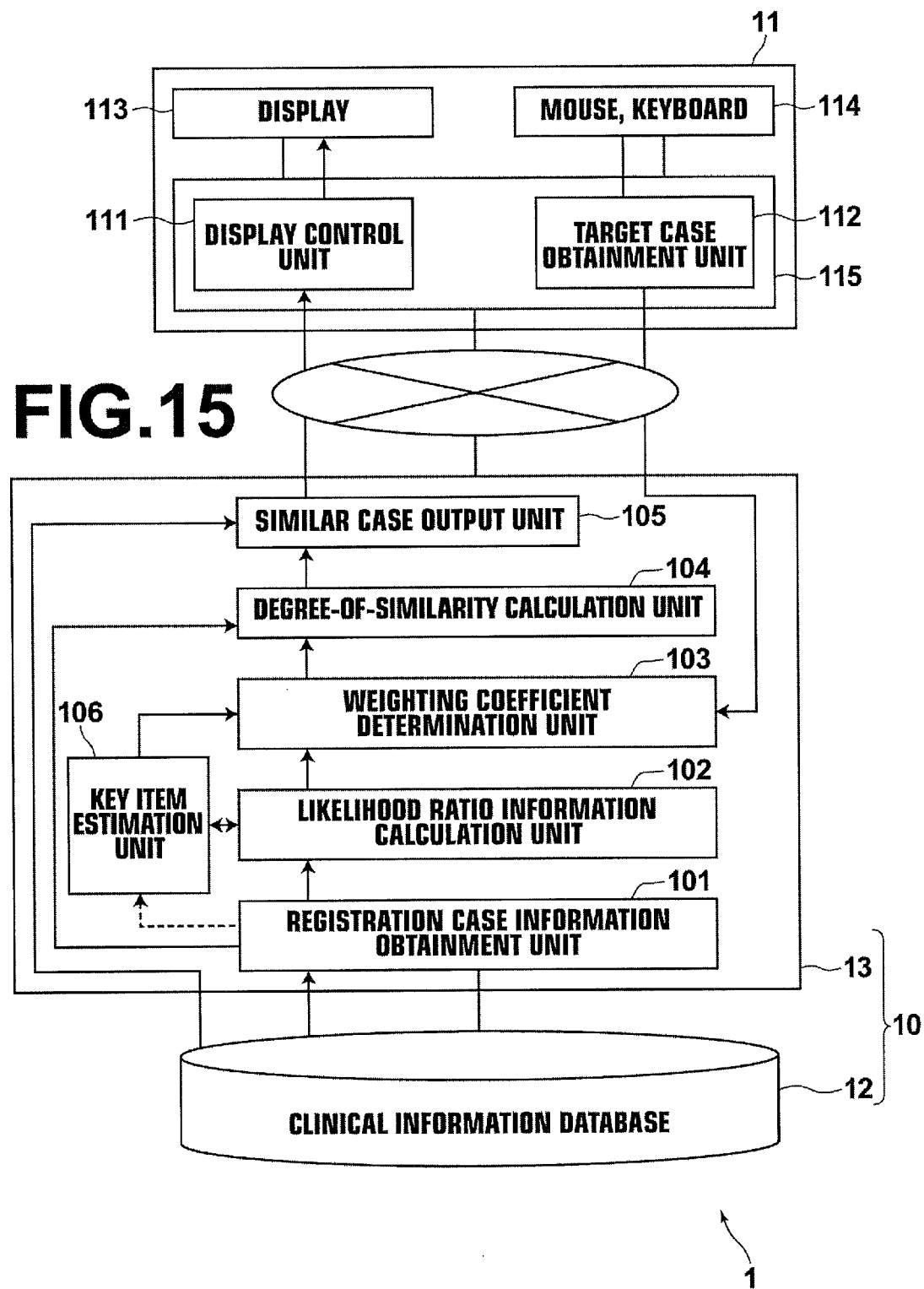
FIG. 15 is a functional block diagram of a clinical information processing apparatus according to the third embodiment.
Figure 16:
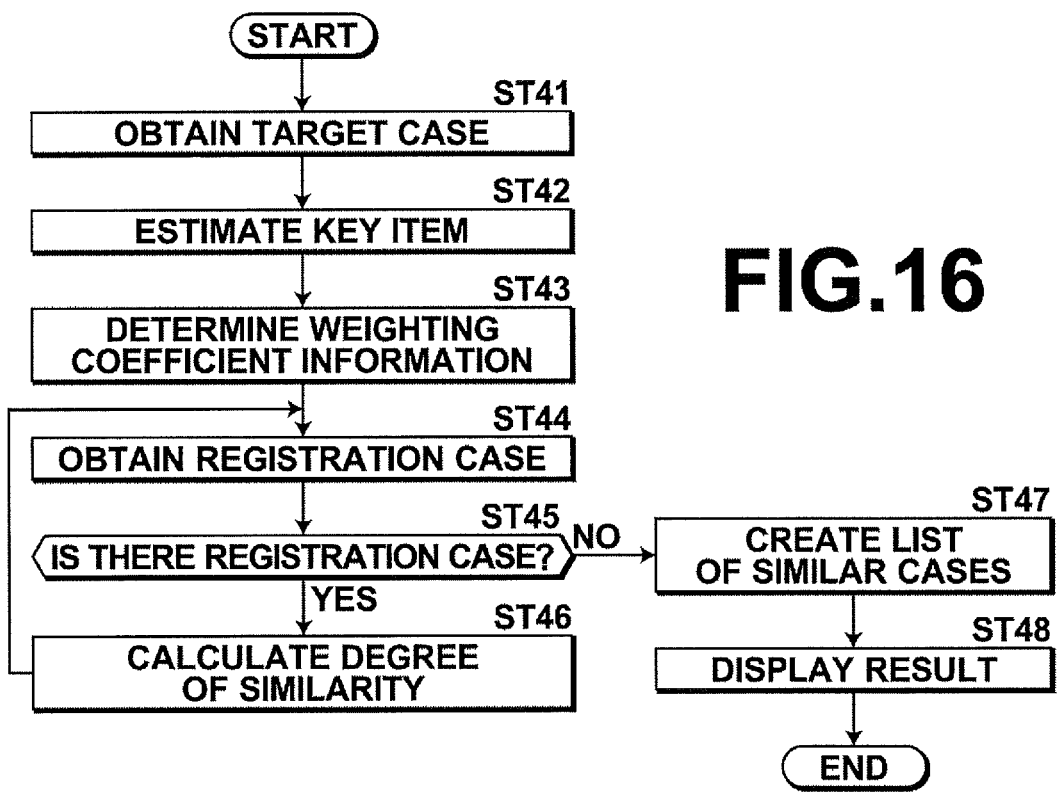
FIG. 16 is a flow chart illustrating a flow of clinical information processing in the third embodiment.

Next, a third embodiment will be described. FIG. 15 is a functional block diagram of the third embodiment. FIG. 16 is a flow chart illustrating a flow of processing in and after obtainment of a clinical-information item of a target patient by the clinical information processing apparatus 1 in the third embodiment. In the third embodiment, steps ST01 through ST06, which are illustrated in FIG. 4, are the same as the first embodiment. Therefore, explanation of steps ST01 through ST06 will be omitted. Features different from the first embodiment will be mainly described, and explanations of the same features as the first embodiment will be omitted.

As illustrated in FIG. 15, the third embodiment differs from the first embodiment in the following points. In the third embodiment, the registration case information obtainment unit 101 further obtains a registration case for estimating a key item. Further, the registration case information obtainment unit 101 includes a key item estimation unit 106 that has the same function as the second embodiment. Further, the weighting coefficient determination unit 103 determines a weighting coefficient based on an item estimated by the key item estimation unit 106.

Next, with reference to FIG. 16, the flow of processing in and after obtainment of a clinical-information item of a target patient by the clinical information processing apparatus 1 in the third embodiment will be described.

First, the target case obtainment unit 112 obtains a clinical-information item of a target patient in a manner similar to the first embodiment (step ST41).

Then, the key item estimation unit 106 calculates, based on the likelihood ratio information illustrated in FIG. 7, a product for each classification of the key item, and the product value is obtained by multiplying a likelihood ratio corresponding to a target classification of each target clinical-information item in a manner similar to step ST22 in Embodiment 2. When the calculated product value satisfies a predetermined threshold condition, it is tentatively estimated that the target patient belongs to the classification of the key item (step ST42). The key item estimation unit 106 in the third embodiment differs from the key item estimation unit 106 in the second embodiment only in that only one classification having the highest overall likelihood ratio is estimated as an estimated disease name in the third embodiment. In the third embodiment, it is assumed that a disease name correlated to the highest overall likelihood ratio is "mycoplasma pneumonia", as illustrated in FIG. 14.

Further, the weighting coefficient determination unit 103 determines a weighting coefficient corresponding to each classification of a clinical-information item or items other than a key item with respect to the estimated classification of the key item. Further, the weighting coefficient determination unit 103 determines each of the weighting coefficients in such a manner that the degree of weighting is higher as the likelihood ratio calculated based on likelihood ratio information is higher. Accordingly, the weighting coefficient determination unit 103 determines weighting coefficient information in which a weighting coefficient corresponding to each classification of a clinical-information or items other than the key item is correlated to the estimated classification of the key item (step ST43).

FIG. 17 is a diagram illustrating an example of weighting coefficient information in the third embodiment. FIG. 18 is a diagram illustrating an example of degree-of-similarity determination information in the third embodiment. The weighting coefficient determination unit 103 calculates, based on the frequency information illustrated in FIG. 7, a weighting coefficient only for a classification of each clinical-information item correlated to the estimated classification of the key item (disease name: mycoplasma) by using a weighting method similar to the first embodiment. Further, the weighting coefficient determination unit 103 determines the calculated weighting coefficient as weighting coefficient information, as illustrated in FIG. 17. In the third embodiment, it is not necessary to calculate weighting coefficients for all classifications of the key item. The weighting coefficient information can be obtained at least by calculating a weighting coefficient only for the estimated classification of the key item. The weighting coefficients in the third embodiment, which are illustrated in FIG. 17, are the same as a bold broken line part in the weighting coefficient information illustrated in FIG. 8.

Next, the registration case information obtainment unit 101 obtains registration cases in a manner similar to step ST13 in the first embodiment, which is illustrated in FIG. 5 (step ST44). If there is a registration case in which a degree of similarity has not been calculated (step ST45 is YES), the degree-of-similarity calculation unit 104 extracts, based on the calculated weighting coefficient information, weighting coefficients that are correlated to the estimated classification of the key item, and that correspond to the classifications of clinical-information items other than the key item. Further, the extracted weighting coefficients are accumulated, and a degree of similarity is calculated (step ST46).

The degree-of-similarity calculation unit 104 generates degree-of-similarity determination information by using the weighting coefficient correlated to the classification of the clinical-information item illustrated in FIG. 17 without regard to a disease name, which is the classification of the key item. FIG. 18 illustrates degree-of-similarity determination information generated based on the registration case information illustrated in FIG. 3 and the weighting coefficient information illustrated in FIG. 17. For example, with respect to age (62 years old) of case 1 registered in the registration case information illustrated in FIG. 3, weighting coefficient of 0 is used. In FIG. 17, the weighting coefficient of 0 is assigned to the classification of the clinical-information item representing age of older than or equal to 40 years old and younger than or equal to 65 years old, and to which the age of case 1 belongs. Further, as illustrated in FIG. 18, the degree-of-similarity calculation unit 104 calculates, as a degree of similarity, a value obtained by accumulating the weighting coefficients corresponding to respective clinical-information items of each case.

In contrast, if there is no registration case in which a degree of similarity has not been calculated (step ST45 is NO), the degree-of-similarity calculation unit 104 sorts the registration cases in the order of degrees of similarity in the same manner as step ST16 illustrated in FIG. 5, and creates a list of similar cases (step ST47). Further, the degree-of-similarity calculation unit 104 displays the list of similar cases in the same manner as step ST17 illustrated in FIG. 4 (step ST48).

According to the third embodiment, it is possible to calculate a degree of similarity for a registration case in which the classification of a key item, such as a disease name, is not known. Therefore, even when the number of registration cases corresponding to a classification of the key item is small, it is possible to calculate a degree of similarity by widening the target of calculation so as to include registration cases in which classification of the key item is not known.

The likelihood ratio information calculation unit 102 may include a likelihood ratio calculation case extraction unit 107 also in the third embodiment in a manner similar to the second embodiment. The likelihood ratio calculation case extraction unit 107 extracts, as a registration case for calculating a likelihood ratio, only a registration case that satisfies a predetermined condition. In this case, the likelihood ratio calculation case extraction unit 107 may extract a registration case for calculating a likelihood ratio based on an arbitrary condition in a manner similar to the second embodiment.

Further, also in the third embodiment, the degree-of-similarity calculation unit may include a degree-of-similarity calculation case extraction unit that extracts, as a registration case for calculating a degree of similarity, only a registration case satisfying a predetermined condition from registration case information. Further, the degree-of-similarity calculation unit may calculate a degree of similarity only based on the extracted registration case for calculating a degree of similarity. In this case, for example, the degree-of-similarity calculation case extraction unit may extract, based on the likelihood ratio information, only a registration case belonging to the classification of each clinical-information item correlated to a likelihood ratio that is greater than or equal to a predetermined threshold value (fifth threshold value).

In the first and third embodiments, when a disease name of a registration case is complications, the degree-of-similarity calculation unit 104 may calculate a degree of similarity for each disease name constituting the complications by obtaining a weighting coefficient corresponding to a clinical-information item other than the key item correlated to complications. Further, the degree-of-similarity calculation unit 104 may obtain the highest one of the calculated degrees of similarity, as a degree of similarity corresponding to the complications.

For example, when a registration case for calculating a degree of similarity is complications of disease name A1 and disease name A2, and each classification of plural clinical-information items (age A4, fever A5, cough A6, sputum A7, and white blood cell number A8) is correlated to the complications, degree A9 of similarity may be calculated with respect to a case in which age A4, fever A5, cough A6, sputum A7, and white blood cell number A8 are correlated to disease name A1. Further, degree A9' of similarity may be calculated with respect to a case in which age A4, fever A5, cough A6, sputum A7, and white blood cell number A8 are correlated to disease name A2. Further, the larger one of the degree A9 of similarity and the degree A9' of similarity may be determined as the degree of similarity of the aforementioned case.

In the first and third embodiments, when the disease name of a registration case is complications, the degree-of-similarity calculation unit 104 may obtain, for each disease name constituting the complications, a weighting coefficient corresponding to each clinical-information item other than a key item correlated to the complications. Further, the degree-of-similarity calculation unit 104 may specify, as a weighting coefficient corresponding to the classification of a clinical-information item, a largest one of weighting coefficients calculated for respective disease names constituting the complications. Similarly, a weighting coefficient may be specified for each classification of each clinical-information item. Further, the degree-of-similarity calculation unit 104 may calculate a degree of similarity by using the specified weighting coefficients.

For example, when a registration case for calculating a degree of similarity is complications of disease name A1 and disease name A1, and each classification (age A4, fever A5, cough A6, sputum A7, and white blood cell number A8) of plural clinical-information items is correlated to the complications, weighting coefficients may be calculated in the following manner. With respect to a case in which age A4, fever A5, cough A6, sputum A7, and white blood cell number A8 are correlated to disease name A1, weighting coefficients B4, B5, B6, B7 and B8 may be calculated for age, fever, cough, sputum and white blood cell number, respectively. Further, with respect to a case in which age A4, fever A5, cough A6, sputum A7, and white blood cell number A8 are correlated to disease name A2, weighting coefficients B4', B5', B6', B7' and B8' may be calculated for age, fever, cough, sputum and white blood cell number, respectively. Further, with respect to the aforementioned case, weighting coefficients to be used for degree-of-similarity determination information may be selected in the following manner. Specifically, the larger one of weighting coefficients B4 and B4' may be used for age, and the larger one of weighting coefficients B5 and B5' may be used for fever. The larger one of weighting coefficients B6 and B6' may be used for cough, and the larger one of weighting coefficients B7 and B7' may be used for sputum. The larger one of weighting coefficients B8 and B8' may be used for white blood cell number.

In the aforementioned case, it is possible to accurately calculate a degree of similarity also for a registration case of complications including complicated clinical-information items. It is possible to extract a similar case from a wide range.

The key item estimation unit 106 in the third embodiment may estimate, as the classification of the key item of a target patient, plural classifications of the key item. In this case, a weighting coefficient for a classification of each clinical-information item may be calculated for each of the estimated plural classifications of the key item. Further, the largest one of the calculated weighting coefficients may be determined as a weighting coefficient corresponding the classification of the specific clinical-information item.

For example, when the key item estimation unit 106 has estimated disease name A1 and disease name A1, as estimated disease names, tentative weighting coefficients are calculated, based on likelihood ratio information, in the following manner. Specifically, with respect to disease name A1, tentative weighting coefficients B4, B5, B6, B7 and B8 are calculated for age, fever, cough, sputum, and white blood cell number, respectively. Similarly, with respect to disease name A2, tentative weighting coefficients B4', B5', B6', B7' and B8' are calculated, based on likelihood ratio information, for age, fever, cough, sputum, and white blood cell number, respectively. Further, the larger one of the tentative weighting coefficients corresponding to the classification of each clinical-information item is determined as weighting coefficient information. For example, when B4>B4', B5>B5', B6>B6', B7>B7', B8<B8', the weighting coefficient information is determined in the following manner. The weighting coefficient is 34 for age, the weighting coefficient is B5 for fever, the weighting coefficient is B6 for cough, the weighting coefficient is B7 for sputum, and the weighting coefficient for white blood cell number is B8'.

In the first through third embodiments, disease names that have been further classified based on the severity of disease may be used as the diagnosis disease name. For example, the severity of a disease included in a registration case may be automatically identified based on a diagnosis guideline or the like that has been prepared in advance. Further, a disease name may be replaced with a disease name obtained by adding the automatically identified severity to the disease name of a registration case before frequency calculation processing. In this case, for example, the disease name "bacterial pneumonia" is replaced with the disease name "severe bacterial pneumonia", and processing for calculating frequency information and likelihood ratio information is performed. Generally, the symptom of the same kind of disease changes depending on the severity of the disease. Therefore, when a detailed disease name that has been further classified based on severity is used as the disease name, as described above, it is possible to determine a weighting coefficient in such a manner to more accurately reflect the characteristic of a disease. Further, it is possible to more appropriately calculate a degree of similarity.

In the first through third embodiments, it is desirable that each disease name is correlated to hierarchical disease names of from a superordinate category through a subordinate category for each type of disease, and stored in the clinical information database 12. It is desirable that the likelihood ratio information calculation unit 102 judges, based on the registration case information for calculating a likelihood ratio, whether there is a disease name in which the number of correlated registration cases is smaller than a predetermined number. If there is such a disease name, it is desirable that the likelihood ratio information calculation unit 102 obtains a superordinate disease name of the disease name, and calculates frequency information and likelihood ratio information for the registration case correlated to the disease name by using the superordinate disease name instead of the disease name. For example, when the number of registration cases of klebsiella pneumonia is small, bacterial pneumonia, which is a superordinate disease name of klebsiella pneumonia, is used as a disease name. When the number of registration cases corresponding a disease name is small, it is impossible to effectively calculate a likelihood ratio. However, when the superordinate name is used, it is possible to use registration cases corresponding to the superordinate name as effective registration cases.

The key item estimation unit may estimate the key item by using an arbitrary method instead of the method used by the key item estimation unit 106 in the second and third embodiments as long as it is possible to estimate a key item based on a clinical-information item of a target patient and a clinical-information item of a comparison target patient. For example, the key item estimation unit 106 may extract a diagnosis image of a past case, and estimate a disease name by performing known image recognition processing on the extracted image.

In the second and third embodiments in the specification of the present invention, only a case including a disease name in the clinical-information item is extracted from the registration case information for calculating a degree of similarity, and the extracted case is used as registration case information for calculating a likelihood ratio. Further, the registration case information for estimating a key item and the registration case information for calculating a likelihood ratio are the same. However, the present invention is not limited to the aforementioned embodiments. The registration case information for estimating a key item, the registration case information for calculating a likelihood ratio, and the registration case information for estimating a key item may be different from each other. Alternatively, they may overlap or coincide with each other. Further, the key item estimation means in the second and third embodiments may estimate a key item by using the frequency information used in likelihood ratio calculation processing. Alternatively, frequency information that is different from the one used in likelihood ratio calculation processing may be generated to estimate a key item.

In the first through third embodiments, the cumulative value of weighting coefficients calculated for each registration case may be directly used as a degree of similarity. Alternatively, the largest value of the cumulative values of weighting coefficients calculated for respective registration cases may be extracted, and a degree of similarity may be normalized by dividing each of the cumulative values of weighting coefficients by the extracted largest value. When the degree of similarity is normalized, it is possible to easily recognize a degree of similarity relative to the highest degree of similarity.

The present invention is not limited the embodiments of the present invention. A part or all of elements of the clinical information processing apparatus may be composed of a workstation. Alternatively, a part or all of the elements of the clinical information processing apparatus may be composed of at least one workstation, a server and a storage device connected through a network. Each device is controlled by a program installed from a recording medium, such as a CD-ROM, and the program performs clinical information processing described in the specification of the present invention. The program may be downloaded from a storage device of a server connected through a network, such as the Internet, and installed.

Each of the aforementioned embodiments has been described only as one of embodiments of the present invention. Therefore, arbitrary modifications and application are possible without deviating from the gist of the present invention.

What is claimed is:

1. A clinical information processing apparatus comprising:
    a memory device which stores a clinical information database including:
        registration case information for calculating a likelihood ratio including a multiplicity of registration cases about a plurality of comparison target patients, and to each of the multiplicity of registration cases a plurality of clinical-information items each of which is classifiable into a plurality of groups being correlated; and
        registration case information for calculating a degree of similarity including a multiplicity of registration cases about a plurality of comparison target patients, and to each of the multiplicity of registration cases a plurality of clinical-information items each of which is classifiable into a plurality of groups being correlated;
    a processing apparatus comprising:
        a target case obtainment unit that obtains, as a target classification of a target clinical item, a classification of each of a plurality of clinical-information items about a target patient; and
        a display control unit;
    a registration case information obtainment unit that accesses the memory device and obtains from the clinical information database the registration case information for calculating a likelihood ratio and the registration case information for calculating a degree of similarity;
    a likelihood ratio information calculation unit that calculates, based on the registration case information for calculating a likelihood ratio, likelihood ratio information for each combination of each classification of a key item of the clinical-information items and each classification of at least one clinical-information item other than the key item and the likelihood ratio information being obtained by calculating a likelihood ratio between a likelihood of belonging to one classification of the key item and a likelihood of belonging to any classification of the key item other than the one classification of the key item when a case belongs to each classification of the at least one clinical-information item other than the key item;
    a weighting coefficient determination unit that calculates, for each of the combinations, values in such a manner that the weight of the value become greater as the likelihood ratio corresponding to the combination is greater, and that determines weighting coefficients by weighting the calculated value in such a manner that a weight of the value corresponding to the target classification is greater than or equal to the weight of the value corresponding to the classification other than the target classification for each of the clinical-information items;
    a degree-of-similarity calculation unit that specifies, based on the determined weighting coefficient information, the weighting coefficient corresponding to each classification of the key item and each classification of at least one clinical-information item other than the key item for each of the registration cases included in the registration case information for calculating a degree of similarity, and that calculates a degree of similarity by using the specified weighting coefficient;
    a similar case output unit that:
        extracts, from among the registration case information for calculating a degree of similarity, the registration case, the calculated degree of similarity of which is higher than a predetermined value, as a similar case, which is similar to the target case;
        retrieves similar case information related to the extracted similar case; and outputs the retrieved similar case information to the display control unit; and
    a display device which is controlled by the display control unit of the processing apparatus, and displays the similar case information.

2. A clinical information processing apparatus, as defined in claim 1, wherein the weighting coefficient determination unit performs weighting in such a manner that the weighting coefficient becomes larger based on the likelihood ratio when the likelihood ratio corresponding the target classification of the target clinical-information item is greater than or equal to a first threshold value, and that the weighting coefficient becomes smaller based on the likelihood ratio when the likelihood ratio corresponding the target classification of the target clinical-information item is less than a second threshold value.

3. A clinical information processing apparatus, as defined in claim 1, wherein the weighting coefficient determination unit performs weighting in such a manner that when a likelihood ratio corresponding the target classification of the target clinical-information item is greater than or equal to a third threshold value and a likelihood ratio corresponding to a classification other than the target classification of the clinical-information item is greater than or equal to the third threshold value, the weighting coefficient corresponding to the classification other than the target classification of the clinical-information item becomes larger based on the likelihood ratios, and that when at least one of the likelihood ratio corresponding the target classification of the target clinical-information item and the likelihood ratio corresponding to a classification other than the target classification of the clinical-information item is less than a fourth threshold value, the weighting coefficient corresponding to the classification other than the target classification of the clinical-information item becomes smaller.

4. A clinical information processing apparatus, as defined in claim 3, wherein the weighting coefficient determination unit performs weighting in such a manner that the weighting coefficient corresponding to the classification other than the target classification of the target clinical-information item becomes a negative value when at least one of the likelihood ratio corresponding the target classification of the target clinical-information item and the likelihood ratio corresponding to the classification other than the target classification of the clinical-information item is less than the fourth threshold value.

5. A clinical information processing apparatus, as defined in claim 1, wherein the weighting coefficient determination unit determines, for each classification of at least a part of the at least one clinical-information item other than the key item, a value obtained by performing logarithmic transformation on the likelihood ratio corresponding to each classification of the at least one clinical-information item other than the key item, as the weighting coefficient.

6. A clinical information processing apparatus, as defined in claim 1, wherein the degree-of-similarity calculation unit includes a degree-of-similarity calculation case extraction unit that extracts, as a registration case for calculating a degree of similarity, only a registration case satisfying a predetermined condition in the registration case information for calculating a degree of similarity, wherein the degree of similarity is calculated only based on the extracted registration case for calculating a degree of similarity.

7. A clinical information processing apparatus, as defined in claim 6, wherein the registration case information obtainment unit further obtains registration case information for estimating a key item, and the registration case information including a multiplicity of registration cases about a plurality of comparison target patients, and to each of the multiplicity of registration cases a plurality of clinical-information items each of which is classifiable into a plurality of groups being correlated,
the apparatus further comprising:
a key item estimation unit that estimates, based on the target classification of the target clinical-information item and the registration case information for estimating a key item, a classification of the key item to which the target patient is estimated to belong,
wherein the degree-of-similarity calculation case extraction unit extracts, as the registration case for calculating a degree of similarity, only the registration case correlated to the classification of the key item estimated by the key item estimation unit from the registration case information for calculating a degree of similarity.

8. A clinical information processing apparatus, as defined in claim 6, wherein the degree-of-similarity calculation case extraction unit extracts, based on the likelihood ratio information, only the registration case in which at least a likelihood ratio corresponding to a classification of each clinical-information item is greater than or equal to a fifth threshold value, as the registration case for calculating a degree of similarity, from the registration cases for calculating a degree of similarity.

9. A clinical information processing apparatus, as defined in claim 6, wherein the degree-of-similarity calculation case extraction unit extracts, based on the likelihood ratio information, only the registration case correlated to a classification of a clinical-information item the likelihood ratio of which is ranked higher than or equal to a predetermined rank in descending order of values, as the registration case for calculating a degree of similarity, from the registration cases for calculating a degree of similarity.

10. A clinical information processing apparatus, as defined in claim 1, wherein the likelihood ratio information calculation unit includes a likelihood ratio calculation case extraction unit that extracts only the registration case satisfying an additional predetermined condition, as the registration case for calculating the likelihood ratio, from the registration case information for calculating a likelihood ratio, and calculates the likelihood ratio information only based on the extracted registration case for calculating the likelihood ratio.

11. A clinical information processing apparatus, as defined in claim 10, wherein the registration case information obtainment unit further obtains registration case information for estimating a key item, and the registration case information including a multiplicity of registration cases about a plurality of comparison target patients, and to each of the multiplicity of registration cases a plurality of clinical-information items each of which is classifiable into a plurality of groups being correlated,
the apparatus further comprising:
a key item estimation unit that tentatively estimates, based on the target classification of the target clinical-information item and the registration case information for estimating a key item, a classification of the key item to which the target patient is estimated to belong,
wherein the likelihood ratio calculation case extraction unit extracts, as the registration case for calculating a likelihood ratio, only the registration case correlated to the classification of the key item estimated by the key item estimation unit from the registration case information for calculating a likelihood ratio.

12. A clinical information processing apparatus comprising:
a memory device which stores a clinical information database including:
registration case information for calculating a likelihood ratio including a multiplicity of registration cases about a plurality of comparison target patients, and to each of the multiplicity of registration cases a plurality of clinical-information items each of which is classifiable into a plurality of groups being correlated;
registration case information for calculating a degree of similarity including a multiplicity of registration cases about a plurality of comparison target patients, and to each of the multiplicity of registration cases a plurality of clinical-information items each of which is classifiable into a plurality of groups being correlated; and
registration case information for estimating a key item including a multiplicity of registration cases about a plurality of comparison target patients, and to each of the multiplicity of registration cases a plurality of clinical-information items each of which is classifiable into a plurality of groups being correlated;
a processing apparatus comprising:
a target case obtainment unit that obtains, as a target classification of a target clinical item, a classification of each of a plurality of clinical-information items about a target patient; and
a display control unit;
a registration case information obtainment unit that access the memory device and obtains from the clinical information database the registration case information for calculating a likelihood ratio and the registration case information for calculating a degree of similarity and the registration case information for estimating a key item;

a likelihood ratio information calculation unit that calculates, based on the registration case information for calculating a likelihood ratio, likelihood ratio information for each combination of classification of a key item of clinical-information items and each classification of at least one clinical-information item other than the key item to each classification of the key item included in the registration cases, and the likelihood ratio information being obtained by calculating a likelihood ratio between a likelihood of belonging to one classification of the key item and a likelihood of belonging to any classification of the key item other than the one classification of the key item when a case belongs to each classification of the at least one clinical-information item other than the key item;

a key item estimation unit that tentatively estimates a classification of the key item to which the target patient is estimated to belong based on the target classification of the target clinical-information information item and the registration case information for estimating a key item;

a weighting coefficient determination unit that calculates, for each of the combinations, values in such a manner that the weight of the value become greater as the likelihood ratio corresponding to the combination is greater, and that determines weighting coefficients by weighting the calculated value in such a manner that a weight of the value corresponding to the target classification is greater than or equal to the weight of the value corresponding to the classification other than the target classification for each of the clinical-information items;

a degree-of-similarity calculation unit that specifies, based on the determined weighting coefficient information, the weighting coefficient corresponding to each classification of the at least one clinical-information items other than the key item for each of the registration cases included in the registration case information for calculating a degree of similarity, and that calculates a degree of similarity by using the specified weighting coefficient;

a similar case output unit that:
  extracts, from among the registration case information for calculating a degree of similarity, the registration case, the calculated degree of similarity of which is higher than a predetermined value, as a similar case, which is similar to the target case;
  retrieves similar case information related to the extracted similar case; and
  outputs the retrieved similar case information to the display control unit; and a display device which is controlled by the display control unit of the processing apparatus, and displays the similar case information.

13. A clinical information processing apparatus, as defined in claim 12, wherein the likelihood ratio information calculation unit includes a likelihood ratio calculation case extraction unit that extracts, as a registration case for calculating a likelihood ratio, only a registration case satisfying an additional predetermined condition from the registration case information for calculating a likelihood ratio, wherein the likelihood ratio information is calculated only based on the extracted registration case for calculating a likelihood ratio.

14. A clinical information processing apparatus, as defined in claim 13, wherein the likelihood ratio calculation case extraction unit extracts, as the registration case for calculating a likelihood ratio, only a registration case correlated to the classification of the key item estimated by the key item estimation unit from the registration case information for calculating a likelihood ratio.

15. A clinical information processing apparatus, as defined in claim 1, wherein each classification of the key item represents a disease name.

16. A clinical information processing apparatus, as defined in claim 15, wherein the degree-of-similarity calculation unit calculates a degree of similarity for each disease name constituting complications by obtaining a weighting coefficient corresponding to each classification of the at least one clinical-information item other than the key item correlated to the complications when the disease name of the registration case is the complications, and obtains a highest one of calculated degrees of similarity, as a degree of similarity corresponding to the complications.

17. A clinical information processing apparatus, as defined in claim 15, wherein the degree-of-similarity calculation unit obtains a weighting coefficient corresponding to each classification of the at least one clinical-information item other than the key item correlated to complications for each disease name constituting the complications when the disease name of the registration case is the complications, and calculates a degree of similarity by using a largest one of weighting coefficients obtained for respective disease names constituting the complications, as a weighting coefficient corresponding to each classification of the at least one clinical-information item other than the key item.

18. A clinical information processing apparatus, as defined in claim 15, wherein the likelihood ratio information calculation unit further obtains a superordinate disease name of the disease name when the number of registration case or cases correlated the disease name is less than a predetermined number based on the registration case information for calculating a likelihood ratio, and calculates the likelihood ratio information by using the superordinate disease name instead of the disease name for the registration case correlated to the disease name.

19. A clinical information processing apparatus, as defined in claim 1, wherein the display control unit displays, based on the calculated degree of similarity, the registration cases as a list in descending order of the degree of similarity in such a manner to include information about the classification of the clinical-information items in which at least one of the likelihood ratio and the weighting coefficient is higher than or equal to a predetermined value for each of the registration cases.

20. A clinical information processing method, the method comprising:
  accessing a memory device which stores a clinical information database, and obtaining from the clinical information database:
    registration case information for calculating a likelihood ratio including a multiplicity of registration cases about a plurality of comparison target patients, and to each of the multiplicity of registration cases a plurality of clinical-information items each of which is classifiable into a plurality of groups being correlated; and
    registration case information for calculating a degree of similarity including a multiplicity of registration cases about a plurality of comparison target patients, and to each of the multiplicity of registration cases a plurality of clinical-information items each of which is classifiable into a plurality of groups being correlated;

in a processing apparatus comprising a target case obtainment unit and a display control unit, obtaining, as a target classification of a target clinical item, a classification of each of a plurality of clinical-information items about a target patient;

calculating, based on the registration case information for calculating a likelihood ratio, likelihood ratio information for each combination of a classification of a key item of the plurality of clinical-information items and each classification of at least one clinical-information item other than the key item to each classification of the key item included in the registration cases, and the likelihood ratio information being obtained by calculating a likelihood ratio between a likelihood of belonging to one classification of the key item and a likelihood of belonging to any classification of the key item other than the one classification of the key item when a case belongs to each classification of the at least one clinical-information item other than the key item;

calculating, for each of the combinations, values in such a manner that the weight of the value become greater as the likelihood ratio corresponding to the combination is greater, and determining weighting coefficients by weighting the calculated value in such a manner that a weight of the value corresponding to the target classification is greater than or equal to the weight of the value corresponding to the classification other than the target classification for each of the clinical-information items;

specifying, based on the determined weighting coefficient information, the weighting coefficient corresponding to each classification of the key item and each classification of at least one clinical-information item other than the key item for each of the registration cases included in the registration case information for calculating a degree of similarity, and calculating a degree of similarity by using the specified weighting coefficient;

extracting, from among the registration case information for calculating a degree of similarity, the registration case, the calculated degree of similarity of which is higher than a predetermined value, as a similar case, which is similar to the target case, retrieving similar case information related to the extracted similar case;

outputting the retrieved similar case information to the display control unit; and displaying the similar case information on a display device which is controlled by the display control unit of the processing apparatus.

21. A non-transitory computer-readable recording medium having stored therein a clinical information processing program for causing a computer to perform a clinical information processing method, the method comprising:

accessing a memory device which stores a clinical information database, and obtaining from the clinical information database:

registration case information for calculating a likelihood ratio including a multiplicity of registration cases about a plurality of comparison target patients, and to each of the multiplicity of registration cases a plurality of clinical-information items each of which is classifiable into a plurality of groups being correlated; and registration case information for calculating a degree of similarity including a multiplicity of registration cases about a plurality of comparison target patients, and to each of the multiplicity of registration cases a plurality of clinical-information items each of which is classifiable into a plurality of groups being correlated;

obtaining, as a target classification of a target clinical item, a classification of each of a plurality of clinical-information items about a target patient;

calculating, based on the registration case information for calculating a likelihood ratio, likelihood ratio information for each combination of a classification of a key item of the plurality of clinical-information items and each classification of at least one clinical-information item other than the key item to each classification of the key item included in the registration cases, and the likelihood ratio information being obtained by calculating a likelihood ratio between a likelihood of belonging to one classification of the key item and a likelihood of belonging to any classification of the key item other than the one classification of the key item when a case belongs to each classification of the at least one clinical-information item other than the key item;

calculating, for each of the combinations, values in such a manner that the weight of the value become greater as the likelihood ratio corresponding to the combination is greater, and determining weighting coefficients by weighting the calculated value in such a manner that a weight of the value corresponding to the target classification is greater than or equal to the weight of the value corresponding to the classification other than the target classification for each of the clinical-information items;

specifying, based on the determined weighting coefficient information, the weighting coefficient corresponding to each classification of the key item and each classification of at least one clinical-information item other than the key item for each of the registration cases included in the registration case information for calculating a degree of similarity, and calculating a degree of similarity by using the specified weighting coefficient extracting, from among the registration case information for calculating a degree of similarity, the registration case, the calculated degree of similarity of which is higher than a predetermined value, as a similar case, which is similar to the target case, retrieving similar case information related to the extracted similar case;

outputting the retrieved similar case information to the display control unit; and displaying the similar case information on a display device.

22. A clinical information processing apparatus as defined in claim 1, further comprising:

a clinical information management server comprising:

a general purpose computer including the registration case information obtainment unit, the likelihood ratio information calculation unit, the weighting coefficient determination unit, and the degree-of-similarity calculation unit; and the clinical information database which stores the registration case information, and is accessible by the registration case information obtainment unit.

23. A clinical information processing apparatus as defined in claim 22, further comprising:

a clinical department terminal which is connected to the clinical information management server via a network, and includes the processing apparatus and the display device.

24. A clinical information processing apparatus as defined in claim 1, wherein the display control unit displays the similar case information on the display device in such a manner that information about the classification of the clinical-information items in which at least one of the likelihood ratio and the weighting coefficient is higher than or equal to a predetermined value for each of the registration cases is included.

25. A clinical information processing apparatus as defined in claim 1, wherein the display control unit displays the similar case information on the display device in such a manner that the classification of the clinical-information items is distinguishable according to the weighting coefficient thereof.

26. A clinical information processing apparatus as defined in claim 1, wherein the classifications of the clinical-information item are groups in which a clinical-information item is classified according to a type or a numerical value range based on a judgment standard in medical diagnosis.

\* \* \* \* \*